United States Patent
Miyawaki et al.

(10) Patent No.: US 6,193,709 B1
(45) Date of Patent: Feb. 27, 2001

(54) ULTRASONIC TREATMENT APPARATUS

(75) Inventors: Makoto Miyawaki, Tanashi; Toshihiko Hashiguchi, Sagamihara; Mitsumasa Okada, Hachioji; Norikiyo Shibata, Yamato, all of (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/310,646

(22) Filed: May 12, 1999

(30) Foreign Application Priority Data

| May 13, 1998 | (JP) | 10-130489 |
| Apr. 16, 1999 | (JP) | 11-109314 |
| Apr. 16, 1999 | (JP) | 11-109315 |
| Apr. 16, 1999 | (JP) | 11-109316 |
| Apr. 16, 1999 | (JP) | 11-109317 |
| Apr. 16, 1999 | (JP) | 11-109318 |

(51) Int. Cl.[7] ............................................ A61B 17/32
(52) U.S. Cl. .................... 606/1; 606/45; 606/49; 606/169; 606/171; 606/205; 601/2; 604/22
(58) Field of Search .................... 601/1–3; 6/32, 6/41–52, 169–171, 205

(56) References Cited

U.S. PATENT DOCUMENTS

| 5,873,873 | * | 2/1999 | Smith et al. | 606/1 |
| 5,980,510 | * | 11/1999 | Tsonton et al. | 606/1 |
| 6,024,750 | * | 2/2000 | Mastri et al. | 606/169 |
| 6,036,667 | * | 3/2000 | Manna et al. | 604/22 |
| 6,068,647 | * | 5/2000 | Witt et al. | 606/205 |

* cited by examiner

Primary Examiner—Linda C. M. Dvorak
Assistant Examiner—David M. Ruddy
(74) Attorney, Agent, or Firm—Frishauf, Holtz, Goodman, Langer & Chick, P.C.

(57) ABSTRACT

An ultrasonic treatment apparatus according to the present invention comprises an ultrasonic transducer for generating ultrasonic vibration, a vibration transmitting member for transmitting the ultrasonic vibration generated by the ultrasonic transducer, the vibration transmitting member having a proximal end connected to the ultrasonic transducer and a distal end portion used to treat a living organism by means of the transmitted ultrasonic vibration, a grasping member opposed to the distal end portion of the vibration transmitting member and having a grasping surface capable of grasping the living organism in cooperation with the distal end portion, an operating mechanism for moving the grasping member between a closed position in which the grasping member engages the distal end portion of the vibration transmitting member and an open position in which the grasping member is separated from distal end portion, and a follow-up mechanism for driving or allowing the grasping member in the closed position to follow a deflective displacement of the distal end portion of the vibration transmitting member so that the substantially whole surface of the grasping surface of the grasping member contacts with the distal end portion of the vibration transmitting member.

24 Claims, 18 Drawing Sheets

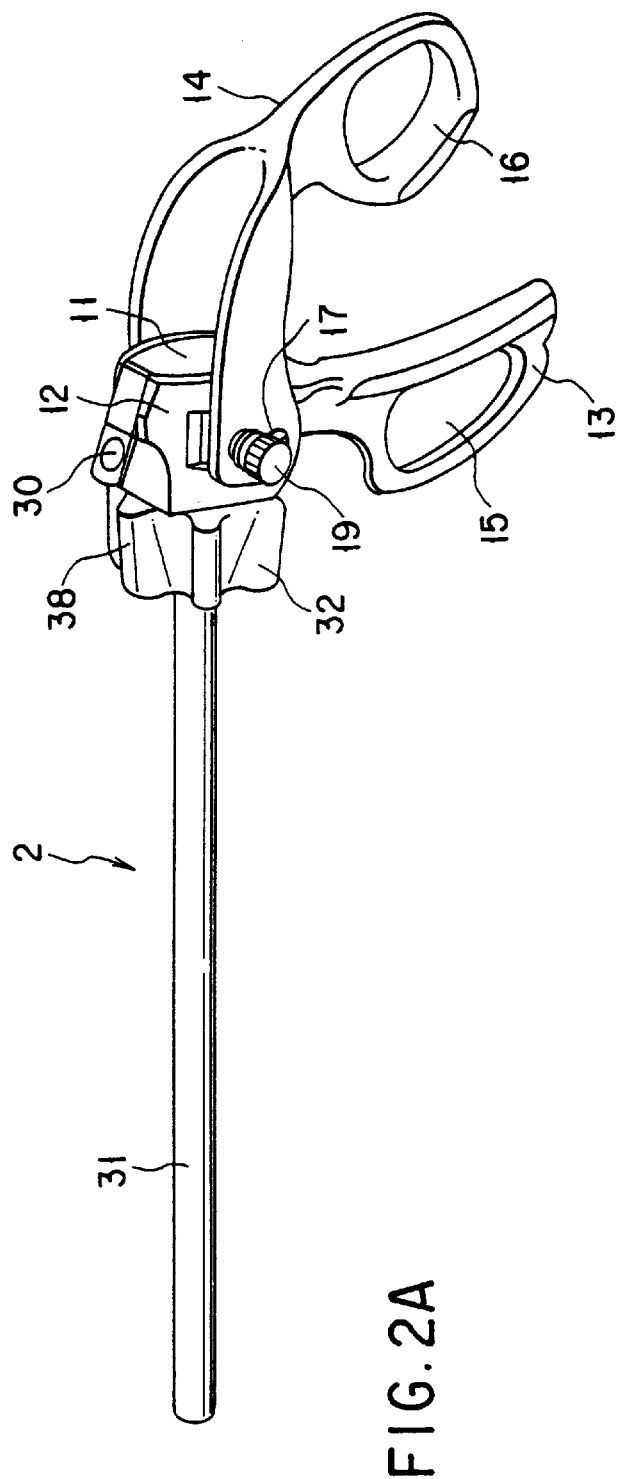
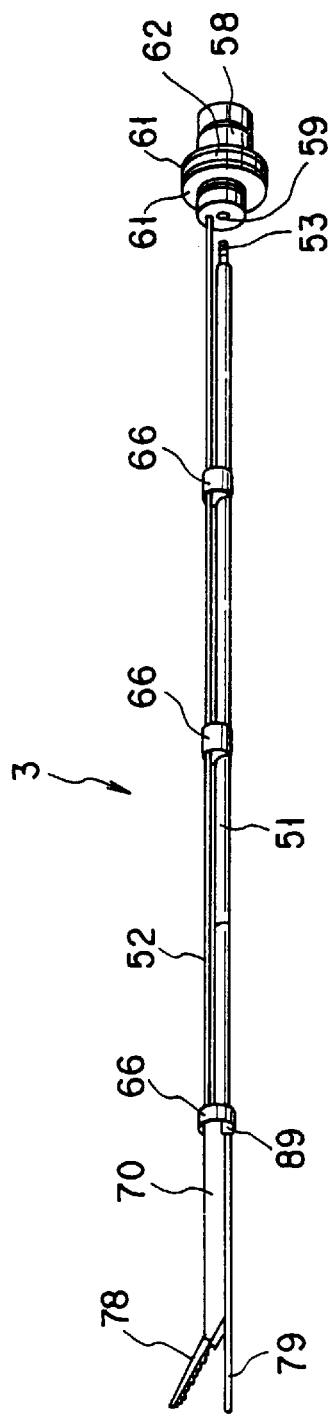
FIG. 2A
FIG. 2B

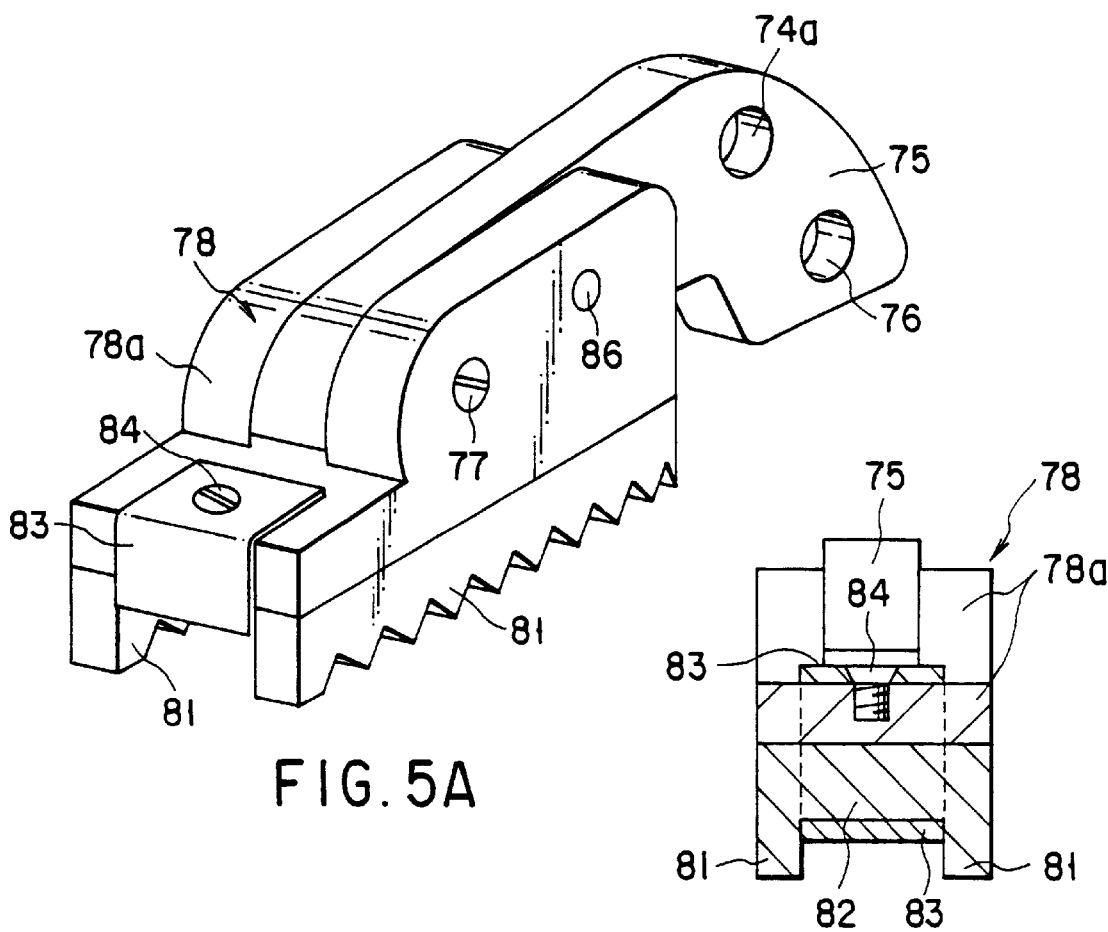
FIG. 5A
FIG. 5B
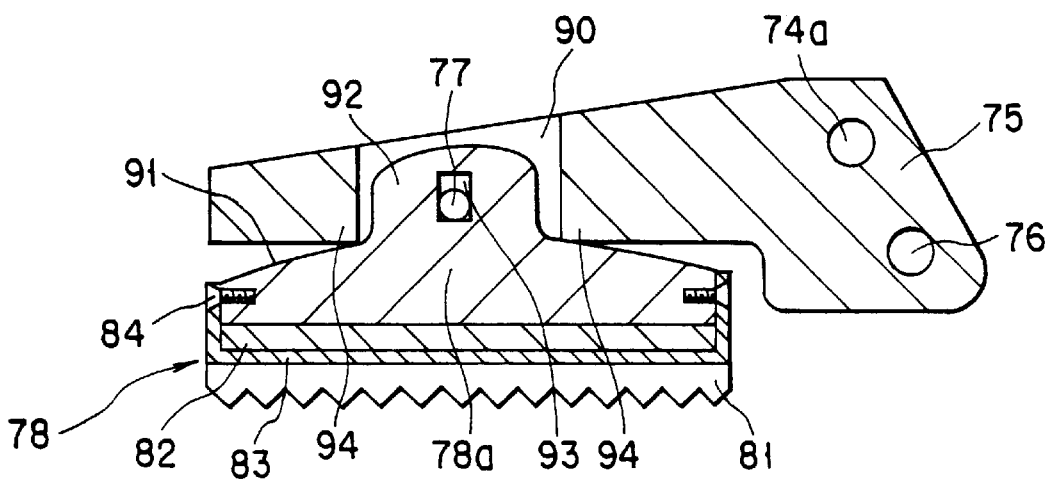
FIG. 6

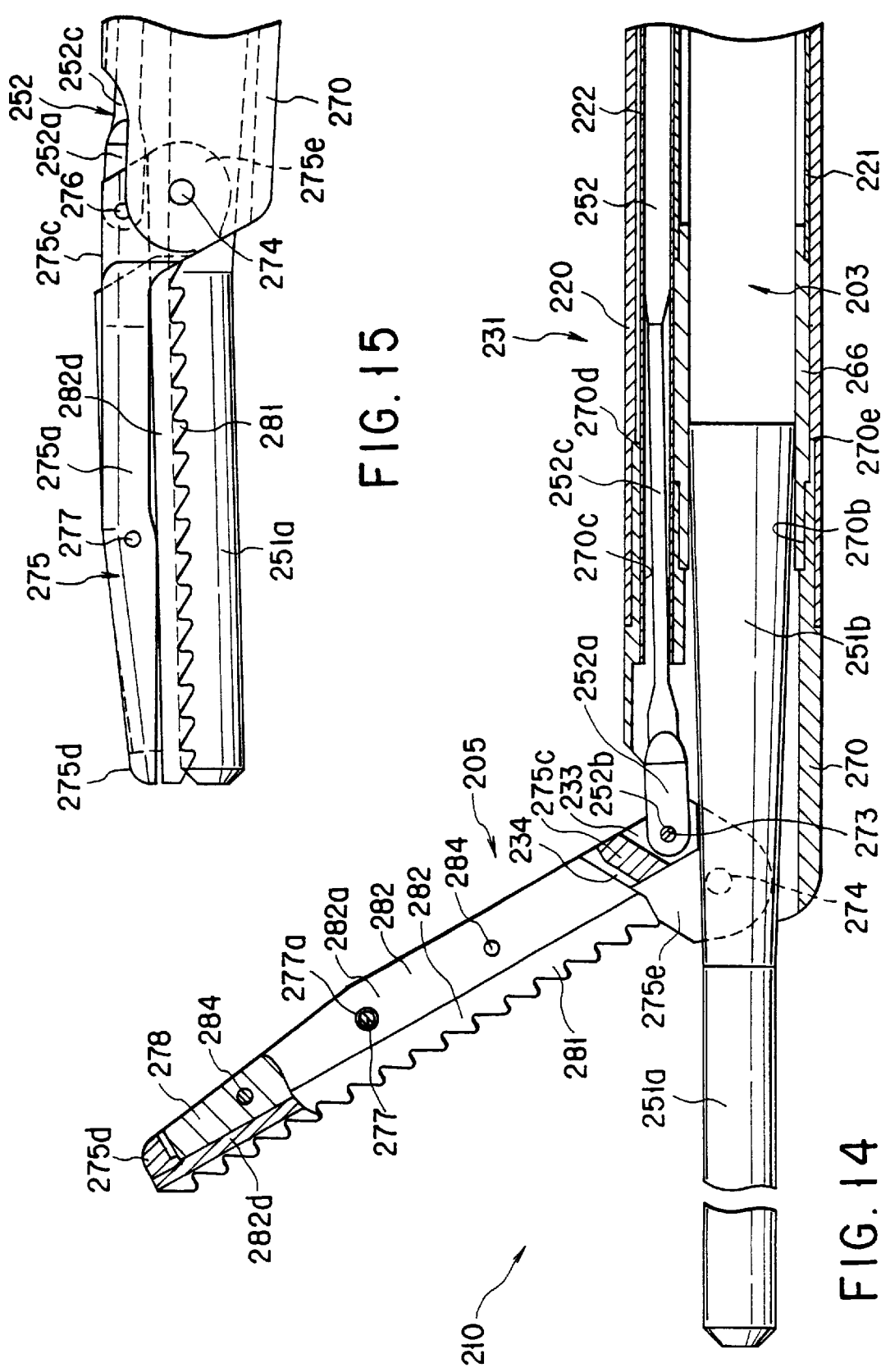

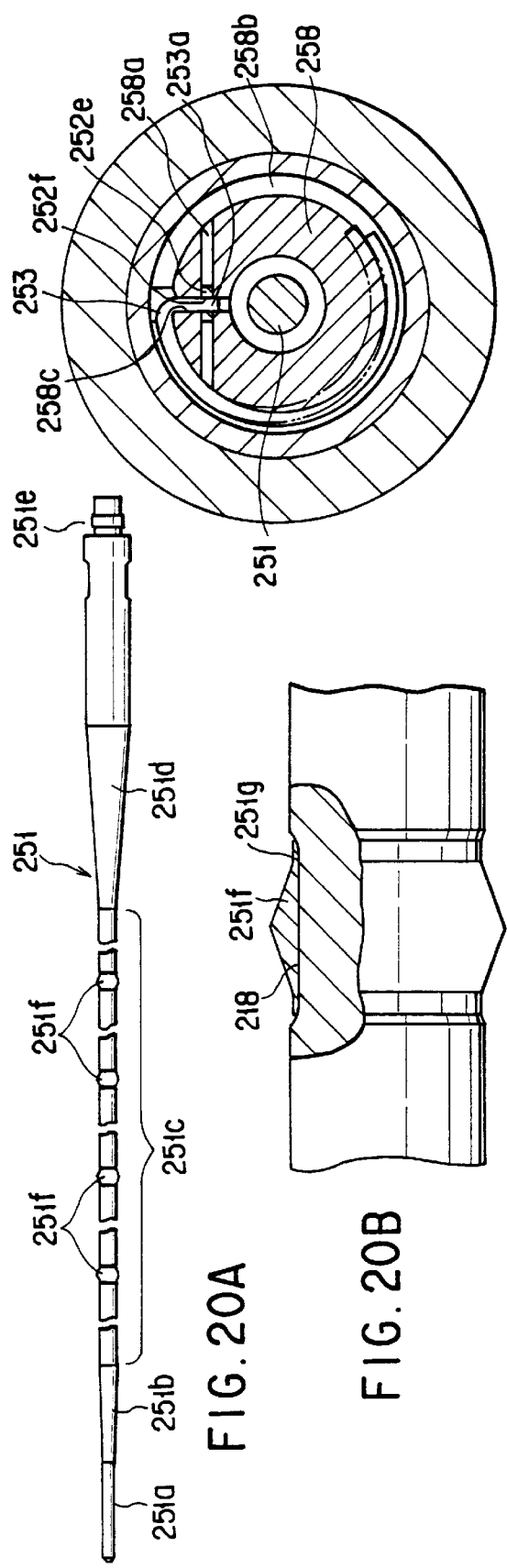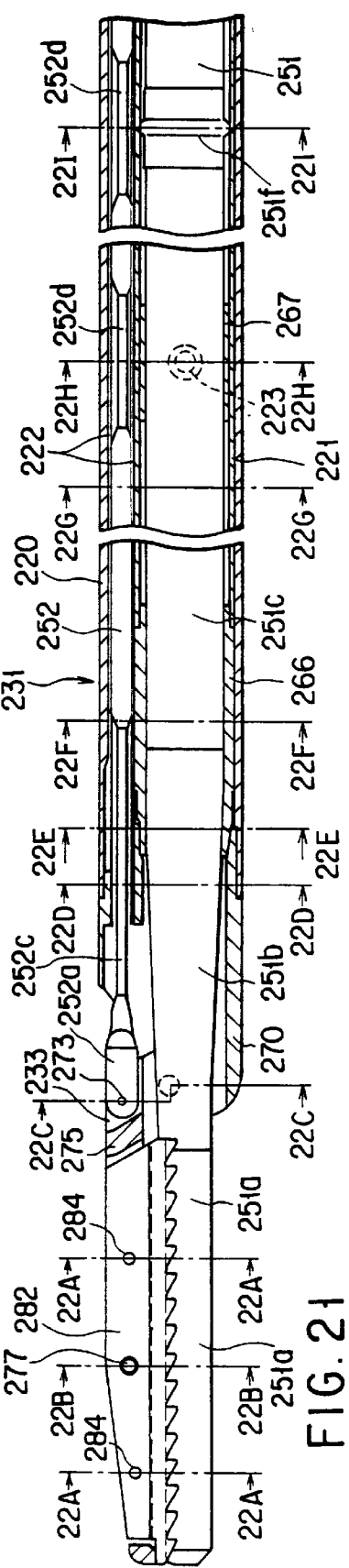

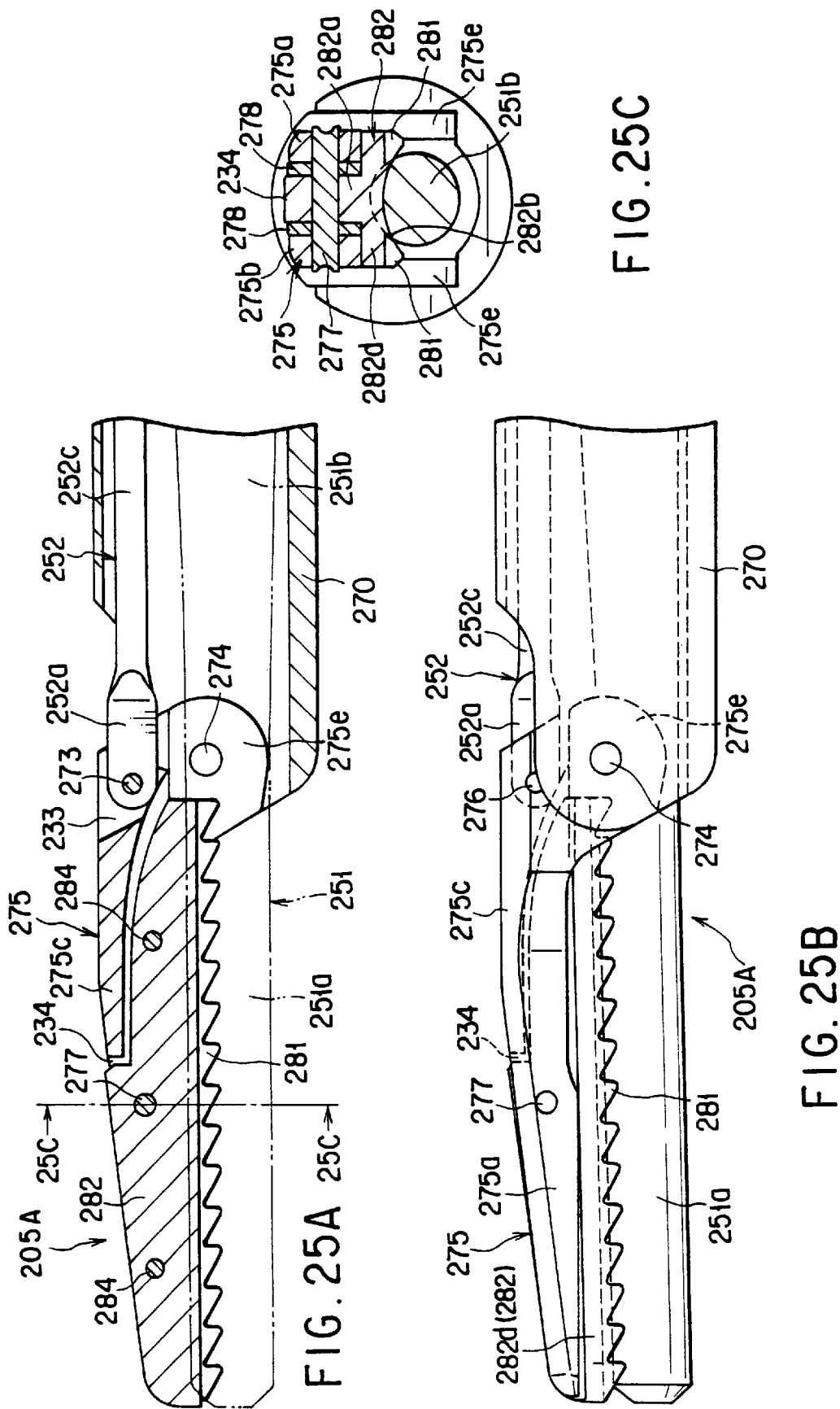

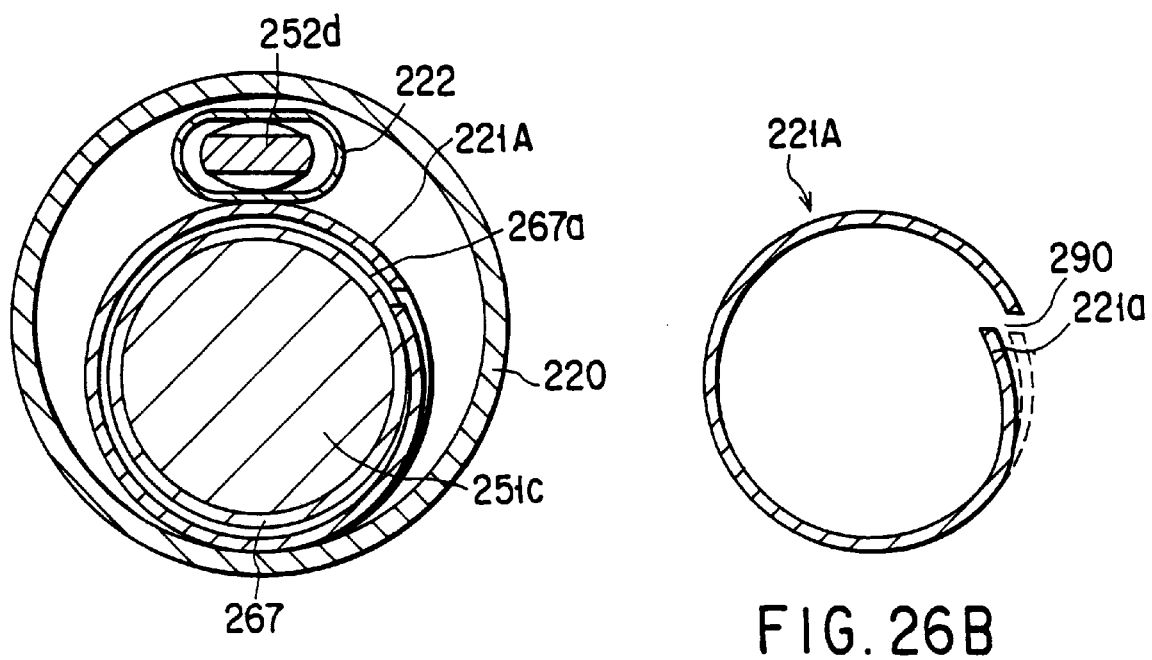
FIG. 26A
FIG. 26B
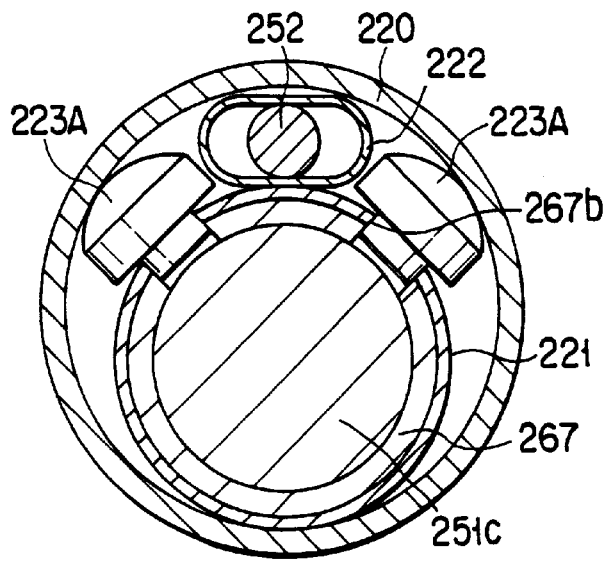
FIG. 27

ULTRASONIC TREATMENT APPARATUS

BACKGROUND OF THE INVENTION

The present invention relates to an ultrasonic treatment apparatus capable of treating an organism with use of frictional heat produced by ultrasonic vibration while grasping the organism.

Conventionally, there are various ultrasonic treatment apparatuses that are used to carry out treatments, such as incision, coagulation, etc., by utilizing the energy of ultrasonic vibration. Among these apparatuses, one that is designed to grasp an organism as it treats it by means of ultrasonic vibration is described in U.S. Pat. No. 5,322,055, for example.

This ultrasonic treatment apparatus comprises a long sheath for use as an insert section. A jaw, a grasping member, is rockably attached to the distal end of the sheath. A vibration transmitting member for transmitting ultrasonic vibration is passed through a first channel that is formed in the sheath. The distal end portion of the transmitting member projects from a distal-end opening of the sheath so as to face the jaw, and serves as an ultrasonic probe that grasps an organism in conjunction with the jaw and treats it by means of ultrasonic vibration.

The jaw is connected to an operating rod that is passed through a second channel in the sheath. As the rod is pushed or pulled, the jaw is rocked between a closed position in which it faces and engages the ultrasonic probe and an open position in which it is separated from the probe.

A mechanism for pushing and pulling the operating rod is provided in an operating section that is situated on the proximal end side of the sheath. More specifically, the operating section is provided with a fixed handle, which is formed integrally therewith, and a movable handle that is rockably attached to the operating section (fixed handle) by means of a pivot. As the movable handle is rocked, the operating rod connected thereto is pushed or pulled. The pivot, a fulcrum for the rocking motion of the movable handle, is situated between a finger plate portion of the movable handle, which serves as a point of application to which an operating force is applied, and a point of action or input portion (junction between the operating rod and the movable handle) for the operating force on the rod. In consideration of the operating efficiency, the jaw is designed to be closed as the movable handle is gripped and moved forward or toward the fixed handle.

Since the ultrasonic probe is formed of the free end of the ultrasonic vibration transmitting member, it is pushed and deflected by the jaw as the organism is held between the probe and the jaw. Accordingly, a gap or noncontact space is formed between the probe and the jaw, so that the coagulation-incision capacity of the apparatus is lowered.

In one case, the jaw is rocked to its closed position by pushing out the operating rod forward. In the other case, it is done by pulling the rod. In the former case, the jaw and the operating rod are connected to each other in a position above a fulcrum for the rocking motion of the jaw or outside the sheath. In the latter case, the jaw and the rod are connected in a position below the fulcrum or inside the sheath. In the latter case, however, a pivot as the fulcrum for the rocking motion of the jaw is inevitably situated on the outer peripheral side portion of the sheath, so that the jaw and the distal end portion of the sheath that supports the jaw cannot maintain high strength and durability. According to the technique described in U.S. Pat. No. 5,322,055, therefore, the jaw is designed to be closed by pushing out the operating rod forward, so that the pivot for the jaw is situated inside the sheath, whereby the strength and durability of the jaw and the distal end portion of the sheath are maintained. In this arrangement, however, the pivot as the fulcrum for the rocking motion of the movable handle is situated between the finger plate portion of the movable handle, which serves as the point of application to which the operating force is applied, and the point of action or input portion for the operating force on the rod. Further, the operating rod is moved forward to close the jaw in a manner such that the movable handle is gripped and moved forward or toward the fixed handle. It is necessary, therefore, to provide a link mechanism for aligning the operating direction for the movable handle with the moving direction of the operating rod. Thus, when the movable handle (finger plate portion) is moved forward, the point of action, which is situated on the opposite side of the fulcrum for the rocking motion of the movable handle from the finger plate portion, moves rearward. Accordingly, it is necessary to provide a link mechanism for converting this rearward movement into a forward movement and transmitting the forward movement to the operating rod. With use of the link mechanism of this type, frictional resistance is produced at the fulcrum of the link and each end of the link by the transmission of force. As the number of kinematic pairs is increased, moreover, regions that require necessary gaps for operation increase, so that backlash enlarges as a whole. As the number of required members increases, furthermore, regions that are subject to elastic deformation also increase, so that various problems are aroused including an increase in the general elastic deformation.

Further, the outer peripheral surface of the vibration transmitting member is provided with a plurality of support pieces that are located corresponding individually to nodes in the ultrasonic vibration. These support pieces serve to hold the transmitting member in the central portion of the first channel and prevent the transmitting member from touching the first channel. If the organism is held between the jaw and the distal end portion of the transmitting member in a manner such that the operating rod is operated to rock the jaw, however, the distal end portion of the transmitting member that is not supported by the support pieces is deflected by a force received from the jaw. In some cases, therefore, the lateral portion of the distal end of the transmitting member that is situated in the sheath may come into contact with the first channel. If the distal end portion is subjected to a substantial lateral force for any reason or other, it is deflected, so that the lateral portion of the distal end of the transmitting member inevitably touches the first channel. In this case, frictional heat is produced as the deflected transmitting member comes into contact with the first channel. Thereupon, some of the vibration energy is wasted in the region concerned, and the temperature of the sheath surface increases. According to U.S. Pat. No. 5,322,055, therefore, receiving members for receiving the deflection of the lateral portion of the distal end of the transmitting member are provided corresponding individually to the leading node of the ultrasonic vibration and a second node next to it. Since the receiving member that is situated corresponding to the second node is formed of an elastic material, however, it is easily deformed in response to the deflection of the transmitting member. Thus, the deflection of the transmitting member cannot be restrained effectively. Accordingly, a gap is formed between the distal end portion of the vibration transmitting member and the jaw, so that the organism cannot be firmly held between them. In consequence, the organism cannot be treated securely.

Further, both the operating rod and the second channel penetrated thereby have a circular cross section. If the rod and the second channel are thus formed having the same sectional shape, the diameter of the second channel must be increased in order to form a gap for cleaning between the rod and the second channel. (If the rod is too thin, the operating force cannot be satisfactorily transmitted to the jaw.) If the diameter of the second channel (gap between the operating rod and the second channel) is enlarged, however, two problems are aroused. First, the operating rod buckles due to the presence of the gap between the rod and the second channel as the rod is pushed forward in the second channel. The other problem is that if the diameter of the second channel is increased in the case where the first and second channels are arranged in the sheath having a limited size, the diameter of the first channel that is penetrated by the vibration transmitting member must be reduced inevitably, so that the diameter of the transmitting member cannot be large enough to secure satisfactory strength. If the diameter of the second channel is reduced in order to avoid these problems, on the other hand, the gap between the operating rod and the second channel cannot be wide enough, so that it is hard to clean the interior of the second channel. In general, moreover, the distal end portion of the vibration transmitting member has a flat or columnar shape, and a grasping surface of the jaw, which is designed to grasp an organism in cooperation with the distal end portion, is flat. In some cases, therefore, the distal end portion of the transmitting member and the jaw may fail to hold the organism in a stable state between them. In the ultrasonic treatment apparatus described in U.S. Pat. No. 5,322,055, moreover, the flat grasping surface of the jaw is formed having V-shaped notch. If the distal end portion of the vibration transmitting member is eccentric or skewed in this case, however, the state of its contact with the grasping surface of the jaw varies to change the state of the grasped organism when the transmitting member is rotated. Thus, a gap is inevitably formed between the distal end portion of the transmitting member and the grasping surface. In some cases, therefore, the organism may not be able to be accurately treated in a desired state.

BRIEF SUMMARY OF THE INVENTION

A first object of the present invention is to provide an ultrasonic treatment apparatus in which a rockable grasping member and the distal end portion of a vibration transmitting member can be pressed against each other without any gap if the distal end portion of the transmitting member is deflected.

A second object of the invention is to provide an ultrasonic treatment apparatus, in which a grasping member for grasping and treating an organism can maintain high strength and durability, and which need not be provided with a mechanism for aligning the operating direction of a movable handle with the moving direction of an operating rod.

A third object of the invention is to provide an ultrasonic treatment apparatus, which can effectively restrain deflection of the distal end portion of a vibration transmitting member without any vibration energy loss, and can grasp and treat an organism securely.

A fourth object of the invention is to provide an ultrasonic treatment apparatus, in which channels to be penetrated by an operating rod can be arranged efficiently in a sheath without causing the rod to buckle and without lowering the efficiency of cleaning in the channels and the strength of a vibration transmitting member.

A fifth object of the invention is to provide an ultrasonic treatment apparatus, capable of treating an organism with good stability and high efficiency while grasping the organism in a good state at all times.

The first object of the invention is achieved by an ultrasonic treatment apparatus constructed as follows. The ultrasonic treatment apparatus according to the invention comprises: an ultrasonic transducer for generating ultrasonic vibration; a vibration transmitting member for transmitting the ultrasonic vibration generated by the ultrasonic transducer, the vibration transmitting member having a proximal end connected to the ultrasonic transducer and a distal end portion used to treat a living organism by means of the transmitted ultrasonic vibration; a grasping member opposed to the distal end portion of the vibration transmitting member and having a grasping surface capable of grasping the living organism in cooperation with the distal end portion; an operating mechanism for moving the grasping member between a closed position in which the grasping member engages the distal end portion of the vibration transmitting member and an open position in which the grasping member is separated from distal end portion; and a follow-up mechanism for driving or allowing the grasping member in the closed position to follow a deflective displacement of the distal end portion of the vibration transmitting member so that the substantially whole surface of the grasping surface of the grasping member contacts with the distal end portion of the vibration transmitting member.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2A is a perspective view of a handle unit of the apparatus of FIG. 1;

FIG. 2B is a perspective view of a probe unit of the apparatus of FIG. 1;

FIG. 5A is a perspective view showing an open-close member and a grasping member of the probe unit of FIG. 2B;

FIG. 5B is a cross-sectional view of the distal end portion of the grasping member of FIG. 5A;

FIG. 6 is a longitudinal sectional view showing an open-close member and a grasping member of a probe unit of an ultrasonic treatment apparatus according to a second embodiment of the invention;

FIG. 14 is a side sectional view of the distal end side of an insertable sheath section of the apparatus of FIG. 12;

FIG. 15 is a side view showing a closed state of a treatment section of the apparatus of FIG. 12;

FIG. 19 is a sectional view taken along line 19—19 of FIG. 17;

FIG. 20A is a side view of a vibration transmitting member constituting the apparatus of FIG. 12;

FIG. 20B is an enlarged sectional view of a support piece portion of the transmitting member of FIG. 20A;

FIG. 21 is a side sectional view of the insertable sheath section of the apparatus of FIG. 12;

FIG. 25A is a sectional view of a distal acting section according to a modification;

FIG. 25B is a side view of the distal acting section of FIG. 25A;

FIG. 25C is a sectional view taken along line 25C—25C of FIG. 25A;

FIG. 26A is a sectional view (corresponding to the position of a cross section along line 22H—22H of FIG. 21) of an insertable sheath section according to a first modification of the way of attaching a spacer to a main channel tube;

FIG. 26B is a sectional view of a main channel tube according to a modification; and FIG. 27 is a sectional view (corresponding to the position of the cross section along line 22H—22H of FIG. 21) of an insertable sheath section according to a second modification of the way of attaching the spacer to the main channel tube.

DETAILED DESCRIPTION OF THE INVENTION

Figure 1:
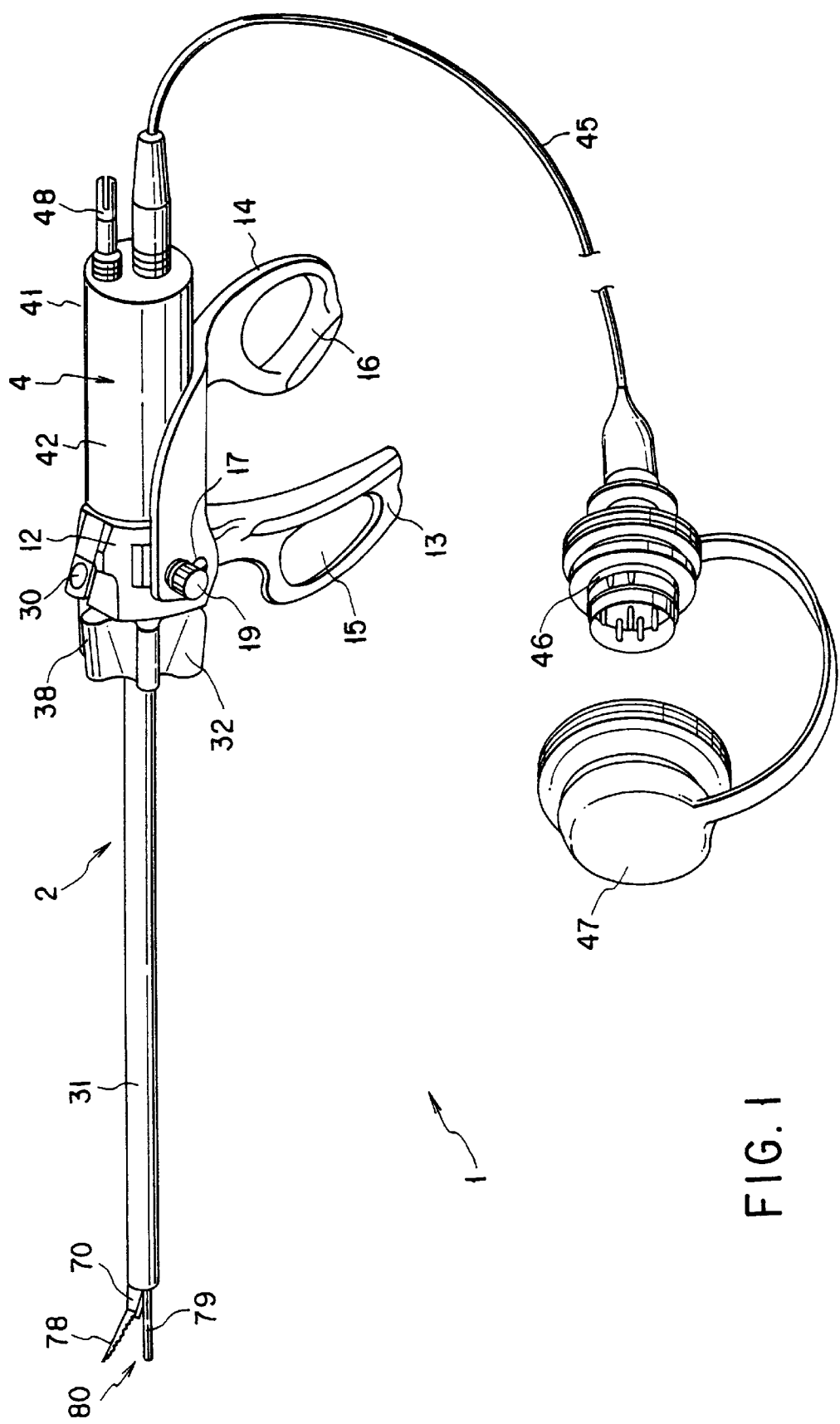
FIG. 1 is a perspective view showing an assembled state of an ultrasonic treatment apparatus according to a first embodiment of the present invention.

Preferred embodiments of the present invention will now be described with reference to the accompanying drawings.

FIGS. 1 to 5 show a first embodiment of the invention. An ultrasonic coagulation-incision apparatus (ultrasonic treatment apparatus) 1 in its assembled state shown in FIG. 1 comprises a handle unit 2, a probe unit 3, and a vibrator unit 4.

As shown in detail in FIG. 2A, the handle unit 2 is provided with an operating section body 12, which includes a vibrator connecting section 11. A fixed front handle 13 and a rockable rear handle 14 are attached to the body 12. An operating end of the front handle 13 is formed having a finger hole 15 in which the other fingers of a hand than the thumb can be inserted. An operating end of the rear handle 14 is formed having a finger hole 16 for the thumb of the same hand. The rear handle 14 is pivotally mounted on the operating section body 12 by means of a pivot pin 17 that is screwed to the body 12. A retaining pin 19 penetrates the front end portion of the rear handle 14. The pin 19 is anchored to a rotor 58 (mentioned later) of the probe unit 3. A stopper piece 30 is pivotally mounted on the upper part of the operating section body 12. The piece 30 serves to fix the probe unit 3, which is attached to the vibrator connecting section 11, in a predetermined set position.

An insertable sheath section 31 is connected to the front end of the operating section body 12. The sheath section 31 can be rotated coaxially with respect to the body 12 by operating a rotary knob 32. The sheath section 31 is treated for electrical insulation. The sheath section 31 contains therein a positioning retaining portion (not shown), which engages the probe unit 3 in a predetermined position in the sheath section 31. The top portion of the knob 32 is marked with an index 38, which indicates the position of the top of the knob.

Figure 3:
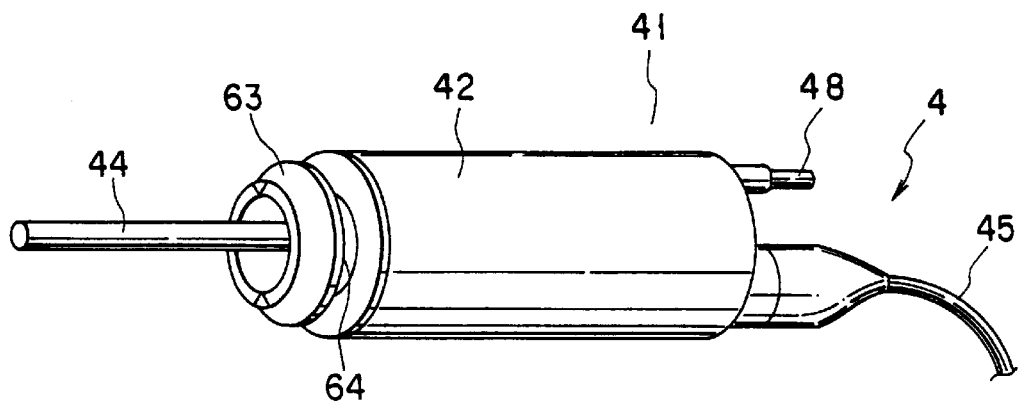
FIG. 3 is a perspective view of a vibrator unit of the apparatus of FIG. 1.

As shown in detail in FIG. 3, the vibrator unit 4 is composed of an ultrasonic transducer (not shown) in a cylindrical cover 42 of a hand piece 41. A horn 44 is connected to the front end of the ultrasonic transducer. An internal-thread portion (not shown) is formed in the distal end portion of the horn 44. An external-thread portion 53 at the rear end portion of a vibration transmitting member 51 (mentioned later) of the probe unit 3 can be screwed into the internal-thread portion. A hand piece cord 45 is connected to the hand piece 41. A hand piece plug 46 is provided on the extended end of the cord 45 (see FIG. 1). A waterproof cap 47 is attached to the plug 46. The hand piece 41 is provided with a high-frequency feeder terminal 48. In carrying out a high-frequency treatment using an end treatment portion of the probe unit 3, high-frequency current is supplied through the terminal 48.

Figure 4:
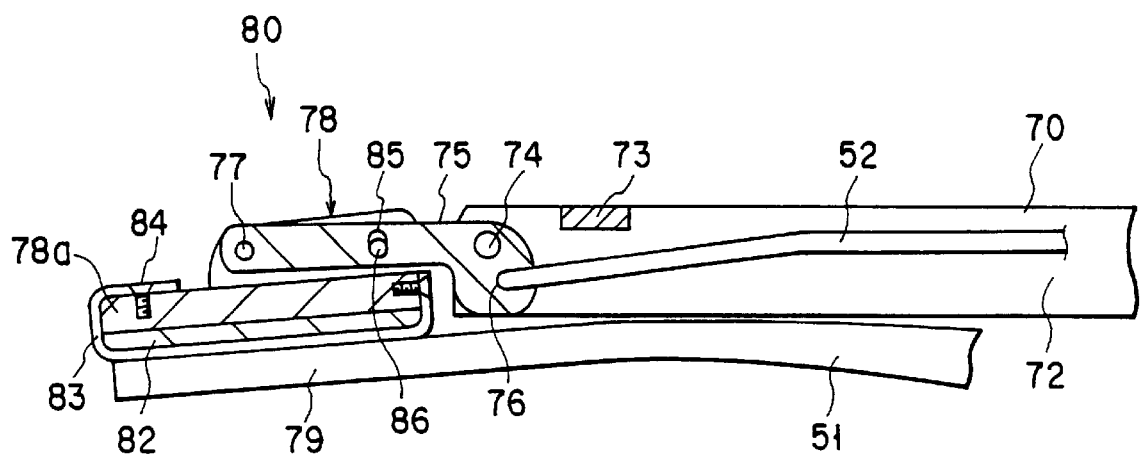
FIG. 4 is a longitudinal sectional view of the distal end portion of the probe unit of the apparatus of FIG. 1.

As shown in detail in FIGS. 2B and 4, the probe unit 3 includes the vibration transmitting member 51, which is a rod-shaped member for transmitting ultrasonic vibration, and an operation drive shaft 52, which extends along and substantially parallel to the member 51. The transmitting member 51 is formed of titanium, aluminum, or some other material that has a high acoustic effect and good adaptability to living organisms. The external-thread portion 53 is formed on the rear end portion of the transmitting member 51. It can be screwed into the internal-thread portion at the distal end of the horn 44 of the vibrator unit 4. The operation drive shaft 52, which is wire-shaped, is formed of stainless steel (SUS) or other material that has relatively high rigidity and elasticity. A cylindrical rotor 58 is fixedly mounted on the rear end of the shaft 52. A center hole 59 is formed in the rotor 58. The hole 59 is situated in line with the central axis of the vibration transmitting member 51. Two collars 61 are arranged on the outer periphery of the rotor 58, and an annular engaging groove 62 is formed between the collars 61. An engaging portion of the retaining pin 19, which is attached to the rear handle 14, a movable-side handle of the handle unit 2, can be fitted in the engaging groove 62.

When the units 2, 3 and 4 are assembled, the front- and rear-side peripheral portions of the rotor 58 are fitted in a fitting hole portion of the handle unit 2 and a bore of a stopper receiving member 63 of the vibrator unit 4 in the operating section body 12, respectively. At the same time, the stopper piece 30 is anchored and connected to a circumferential groove 64 of the receiving member 63 of the vibrator unit 4. In this assembled state, the vibrator unit 4 can rotate integrally with the probe unit 3. By rocking the rear handle 14, moreover, the operation drive shaft 52 of the probe unit 3 can be axially moved back and forth with respect to a stationary member of the vibrator unit 4, which is connected integrally with the rotor 58, and the transmitting member 51.

As shown in FIG. 2B, the vibration transmitting member 51 is connected to the operation drive shaft 52 by means of a plurality of spacers 66. Each spacer 66 is situated corresponding to a node in vibration of the transmitting member 51. More specifically, the spacers 66 are fitted individually on intermediate portions of the transmitting member 51 to support the drive shaft 52 for sliding motion, whereby the member 51 and the shaft 52 are kept spaced and parallel to each other.

As shown in FIG. 4, the leading spacer 66 forms a holding member 70, which extends ahead of the nodes in vibration. Since the leading spacer 66 and the holding member 70 are formed integrally with each other, the member 70 is restrained from moving in the axial direction of the vibration transmitting member 51 and from rocking around the axis of the member 51. The holding member 70 extends close to the distal end of the transmitting member 51. It is formed having a slit 72, which extends from its rear end portion to its distal end. A reinforcing bridge 73 is provided on the distal end portion of the member 70. The bridge 73 connects those regions of the member 70 which are divided right and left by the slit 72. A first pivot pin 74 is provided on the distal end portion of the holding member 70 so as to be situated on the distal end side of the bridge 73 and cross the slit 72. The pin 74 is fitted with a rockable (pivotable) open-close member 75, which is located in the slit 72.

As shown in FIG. 5A, the open-close member 75 is provided with a pivot hole 74a that is penetrated by the first pivot pin 74. The hole 74a is situated in an intermediate position that is biased to the rear end side of the member 75. The member 75 is formed having an engaging hole 76, which is fitted with the distal end of the operation drive shaft 52. The hole 76 is situated on the rear end side of the pivot pin 74. The distal end portion of the open-close member 75 projects forward beyond the distal end of the holding member 70. A grasping member 78 is rockably mounted on the distal end portion of the member 75 by means of a second pivot pin 77. In this case, the first and second pivot pins 74 and 77 are arranged parallel to each other. In a normal attitude, the pins 74 and 77 are located horizontally so that the open-close member 75 and the grasping member 78 can rock up and down within a vertical plane. As shown in FIG. 4, moreover, an ultrasonic probe (blade) 79, which is formed of the distal end portion of the transmitting member 51, is located opposite the member 78. The probe 79 constitutes an openable grasping section 80, which can grasp a living organism in cooperation with the grasping member 78. The probe 79 transmits ultrasonic waves to the grasped organism and treats it.

As shown in FIGS. 4, 5A and 5B, the ultrasonic coagulation-incision apparatus 1 according to the present embodiment is provided with a mechanism for driving the grasping member 78 to move following a deflective displacement of the ultrasonic probe 79. This mechanism is generally formed by rockably mounting the grasping member 78 on the open-close member 75 by means of the second pivot pin 77, as mentioned before. The following is a detailed description of this mechanism.

As shown in FIGS. 5A and 5B, the grasping member 78 includes a body portion 78a or a jaw of a metallic material and two resin tooth portions 81 provided individually on the opposite sides of the undersurface of the body portion 78a. The member 78 further includes a resin intermediate portion 82 connecting the tooth portions 81 and a plate 83 that fixes the intermediate portion 82 by pressing it against the body portion 78a. The plate 83 forms a grasping surface of the grasping member 78 that comes into contact with the organism and grasps it in cooperation with the ultrasonic probe 79. The plate 83 is fixed to the body portion 78 a of the member 78 by means of a setscrew 84. As shown in FIG. 4, the open-close member 75 is penetrated by an arcuate slot 85 across its width. The slot 85 extends in a circular arc around the second pivot pin 77. The slot 85 is engagedly penetrated by a limiting pin 86 that is attached to the grasping member 78. Accordingly, the member 78 is allowed to rock only for the length of the slot 85 around the pin 77. Thus, the slot 85 and the pin 86 constitute rocking restricting means for limiting the range of the relative rocking motions of the open-close member 75 and the grasping member 78. The width of the slot 85 is adjusted so that the limiting pin 86 that is in engagement with the slot 85 can move along the slot 85. It is to be understood that the slot 85 may be formed having a straight shape in place of the arcuate shape only if the pin 86 can move along it. Alternatively, the grasping member 78 may be provided with the slot 85 and the open-close member 75 may be provided with the limiting pin 86.

The following is a description of the operation of the ultrasonic coagulation-incision apparatus 1 constructed in this manner.

If the rear handle 14 of the handle unit 2 is rocked, the operation drive shaft 52 of the probe unit 3 moves forward or rearward, whereupon the open-close member 75 causes the grasping member 78 to rock, basically. Thus, the grasping section 80 is opened or closed. In coagulating or incising the living organism by means of the ultrasonic coagulation-incision apparatus 1, therefore, the organism is positioned between the grasping member 78 and the probe 79, and in this state, the rear handle 14 is rocked to pull the drive shaft 52 in the axial direction. Thereupon, the open-close member 75 rocks in the counterclockwise direction of FIG. 4 around the first pivot pin 74, so that the grasping member 78 moves toward the probe 79. This action causes the living organism to be sandwiched between the member 78 and the probe 79. As this is done, the probe 79 is deflected downward by a force of pressure from the member 78. In consequence, a gap is formed between the grasping member 78 and the top surface of the probe 79. Since the member 78 rocks around second pivot pin 77 with respect to the open-close member 75, however, the gap to be formed between the member 78 and the top surface of the probe 79 is removed, so that the member 78 and the probe 79 are pressed against each other throughout the length for their contact. Thus, the grasping member 78 is always pressed vertically against the probe 79, so that it can uniformly grasp the living organism without leaving any gap. If the probe 79 is subjected to ultrasonic vibration in this state, the grasped organism is coagulated as it is incised.

In the ultrasonic coagulation-incision apparatus 1 according to the present embodiment, as described above, the grasping member 78 moves following the deflective displacement of the ultrasonic probe 79. Therefore, the member 78 and the probe 79 can be pressed against each other without any gap between their respective contact surfaces. Thus, satisfactory coagulation-incision capacity can be secured throughout the respective contact surfaces of the member 78 and the probe 79. Further, the rocking motion of the grasping member 78 with respect to the open-close member 75 is restricted by the slot 85 and the limiting pin 86 to a minimum range such that the deflection of the probe 79 can be absorbed. In consequence, the grasping member 78 never undergoes an unreasonable backlash.

Figure 7:
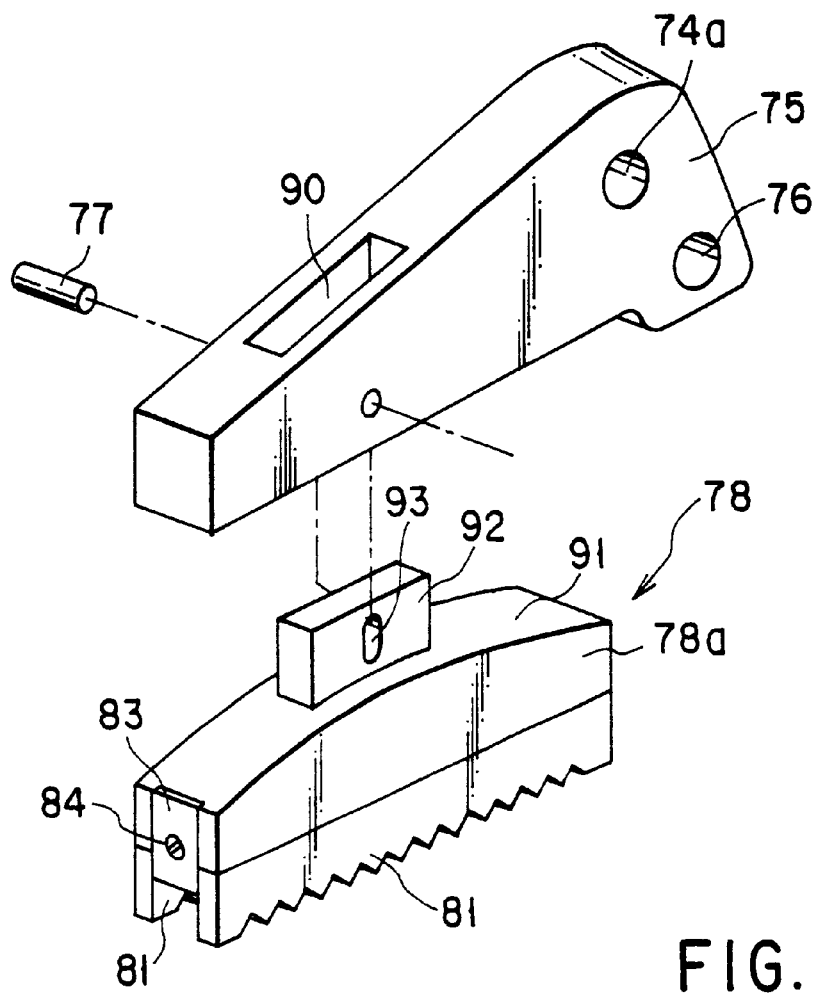
FIG. 7 is an exploded perspective view of the open-close member and the grasping member shown in FIG. 6.

FIGS. 6 and 7 show a second embodiment of the invention. Like reference numerals are used to designate like components common to the first and second embodiments, and a description of those components is omitted.

In the present embodiment, an open-close member 75 is vertically penetrated by a slot 90. A grasping member 78 includes a curved back surface 91 and a rectangular-profiled projection 92 that protrudes from the surface 91. The projection 92 is slidably fitted in the slot 90. In this case, the projection 92 is fitted in the slot 90 in a manner such that it cannot move from side to side although it can move up and down. When the projection 92 is fitted in the slot 90, it is rockably mounted on the second pivot pin 77 that extends across the slot 90. The projection 92 has a slot 93 that is penetrated by the pin 77. The slot 93 is elongated vertically, and its width is substantially equal to the diameter of the pin 77. For other components, the second embodiment is constructed in the same manner as the first embodiment.

According to this arrangement, the grasping member 78 can vertically move and rock within one and the same plane, so that it can move following the deflective displacement of the ultrasonic probe 79. The movement of the open-close member 75 is restricted as its curved back surface 91 engages an open edge portion 94 of the slot 90. Thus, the second embodiment can enjoy the same functions and effects of the first embodiment. In the present embodiment, moreover, the ranges of movement and rocking motion of the grasping member 78 with respect to the open-close member 75 are settled depending on the respective shapes of the back surface 91 and the slot 90 and the length of the slot 93.

Figure 8:
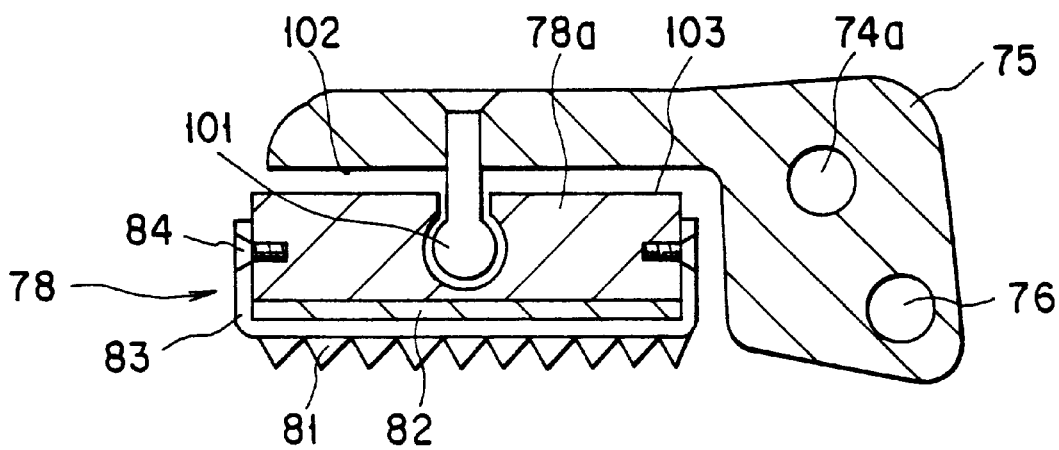
FIG. 8 is a longitudinal sectional view showing an open-close member and a grasping member of a probe unit of an ultrasonic treatment apparatus according to a third embodiment of the invention.

FIG. 8 shows a third embodiment of the invention. Like reference numerals are used to designate like components common to the first and second embodiments, and a description of those components is omitted.

In the present embodiment, a grasping member 78 is pivotally attached to an open-close member 75 by means of a ball joint 101 so that it can move following the deflective displacement of the ultrasonic probe 79. More specifically, the grasping member 78 is provided with a spherical engaging portion (the ball joint 101 ) and the open-close member 75 is provided with a spherical receiving portion capable of receiving and engaging the engaging portion. The member 78, having a back surface 103, is located in a recess 102 in the member 75. The rocking motion of the grasping member 78 with respect to the open-close member 75 is restricted as the back surface 103 engages the top wall surface of the recess 102. For other components, the third embodiment is constructed in the same manner as the first embodiment.

If the probe 79 is deflected downward by a force of pressure from the grasping member 78 with a living organism sandwiched between the member 78 and the probe 79, according to this arrangement, the member 78 rocks around the ball joint 101 with respect to the open-close member 75 lest gap be formed between the probe 79 and the member 78, so that the organism can be uniformly grasped by the grasping section 80 without any gap. Thus, the third embodiment can enjoy the same functions and effects of the first embodiment. In the present embodiment, moreover, the grasping member 78 can move in all directions around the ball joint 101, so that a gap attributable to a deflection of the probe 79 in its twisting direction, as well as a gap attributable to the downward deflection of the probe 79, can be removed. In the present embodiment, the open-close member 75 is provided with the ball joint 101 and the body portion 78 a of the grasping member 78 is provided with the spherical receiving portion for receiving the joint 101. Alternatively, however, the body portion 78a of the grasping member 78 may be provided with the joint 101 and the open-close member 75 may be provided with the receiving portion.

Figure 9:
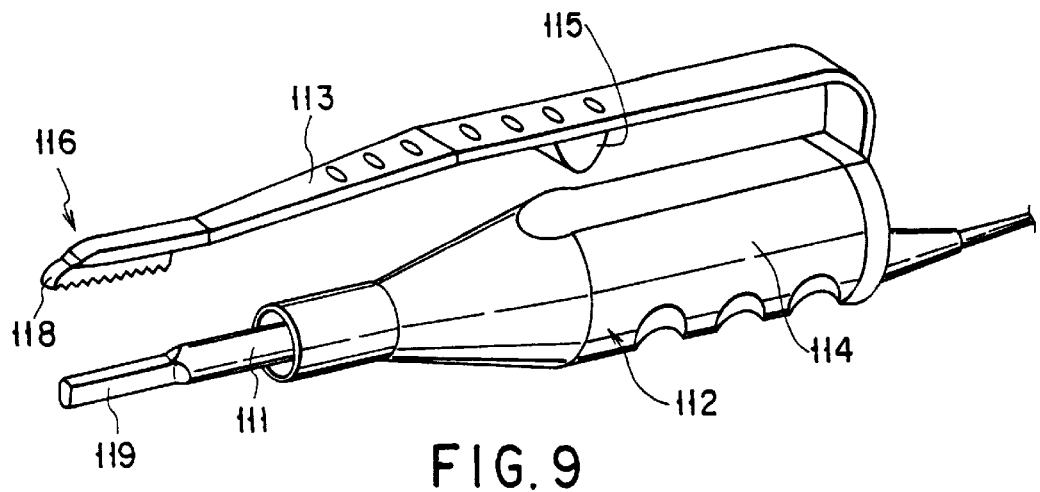
FIG. 9 is a perspective view of an ultrasonic treatment apparatus according to a fourth embodiment of the invention.
Figure 10:
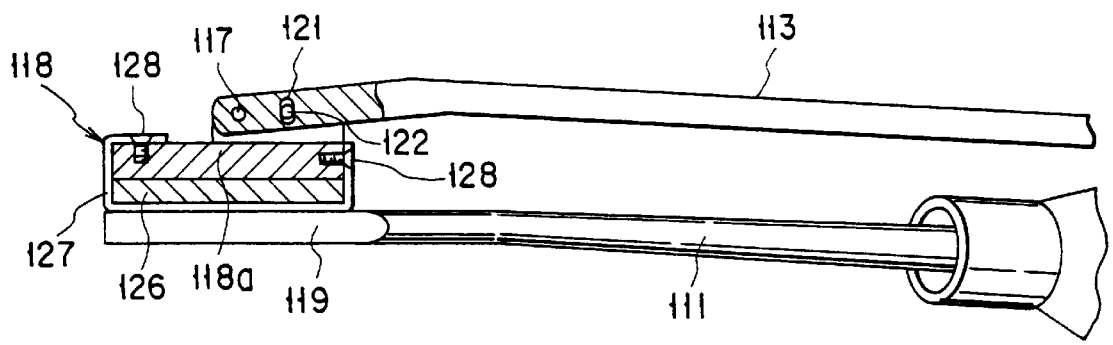
FIG. 10 is a longitudinal sectional view of the distal end portion of the apparatus of FIG. 9.
Figure 11:
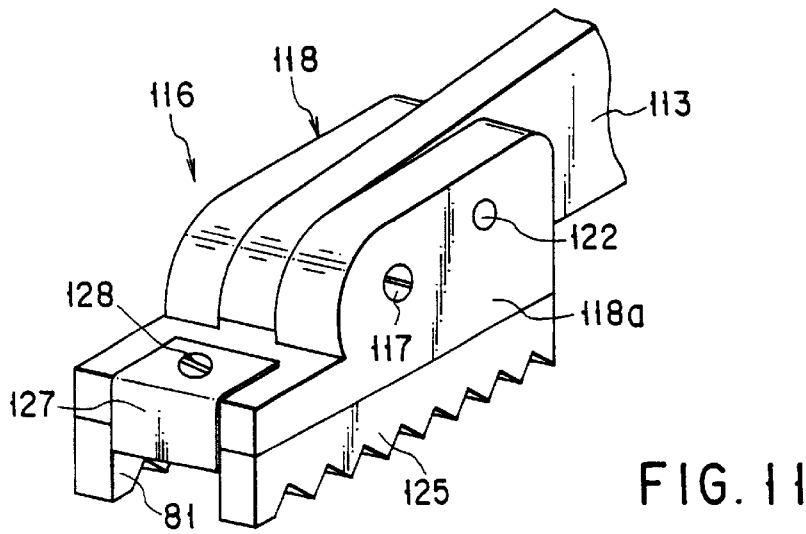
FIG. 11 is a perspective view of a grasping section of the apparatus of FIG. 9.

FIGS. 9, 10 and 11 show a fourth embodiment of the invention.

As shown in FIG. 9, an ultrasonic treatment apparatus according to the present embodiment comprises a vibrator unit 112 that includes an ultrasonic transmitting member 111. One end portion of an operating arm 113, for use as an open-close member, is attached to a body portion 114 of the unit 112. The other end portion of the arm 113 is an elastic free end portion. If the arm 113 is depressed downward with a finger or fingers of a hand that grasps the body portion 114 of the vibrator unit 112, therefore, the arm 113 bends elastically. A stopper 115 protrudes from the undersurface of a substantially central portion of the operating arm 113. The stopper 115 restricts a downward curvature of the arm 113 by engaging the body portion 114 of the vibrator unit 112. A grasping section 116 is provided on the distal end of the free end portion of the arm 113.

As shown in detail in FIGS. 10 and 11, the grasping section 116 includes a grasping member 118 that is rockably mounted on the distal end portion of the operating arm 113 by means of a pivot pin 117. Underlying the member 118, an ultrasonic probe (blade) 119, which is formed of the distal end portion of the vibration transmitting member 111, is opposed to the member 118. The probe 119 constitutes an openable grasping section, which can grasp a living organism in cooperation with the grasping member 118. The probe 119 transmits ultrasonic waves to the grasped organism and treats it.

The ultrasonic coagulation-incision apparatus according to the present embodiment is provided with a mechanism for driving the grasping member 118 to move following a deflective displacement of the ultrasonic probe 119. This mechanism is generally formed by rockably mounting the grasping member 118 on the operating arm 113 by means of the pivot pin 117, as mentioned before. The following is a detailed description of this mechanism.

The grasping member 118 includes a body portion 118a or a jaw of a metallic material and two resin tooth portions 125 provided individually on the opposite sides of the undersurface of the body portion 118a. The member 118 further includes a resin intermediate portion 126 connecting the tooth portions 125 and a plate 127 that fixes the intermediate portion 126 by pressing it against the body portion 118a. The plate 127 forms a grasping surface of the grasping member 118 that comes into contact with the organism and grasps it in cooperation with the ultrasonic probe 119. The plate 127 is fixed to the body portion 118a of the member 118 by means of a setscrew 128. The operating arm 113 is penetrated by an arcuate slot 121 across its width. The slot 121 extends in a circular arc around the pivot pin 117. The slot 121 is engagedly penetrated by a limiting pin 122 that is attached to the grasping member 118. Accordingly, the member 118 is allowed to rock only for the length of the slot 121 around the pin 117. Thus, the slot 121 and the pin 122 constitute rocking restricting means for limiting the range of the relative rocking motions of the operating arm 113 and the grasping member 118. The width of the slot 121 is adjusted so that the limiting pin 122 that is in engagement with the slot 121 can move along the slot 121. It is to be understood that the slot 121 may be formed having a straight shape in place of the arcuate shape only if the pin 122 can move along it.

If the arm 113 is depressed downward with a finger or fingers of a hand that grasps the body portion 114 of the vibrator unit 112, according to this arrangement, the arm 113 bends elastically, so that the grasping section 116 approaches the probe 119. This action causes the living organism to be sandwiched between the grasping member 118 and the probe 119. As this is done, the probe 119 is deflected downward by a force of pressure from the member 118. In consequence, a gap is formed between the grasping member 118 and the top surface of the probe 119. Since the member 118 rocks around second pivot pin 117 with respect to the operating arm 113, however, the gap to be formed between the member 118 and the top surface of the probe 119 is removed, so that the member 118 and the probe 119 are pressed against each other throughout the length for their contact. Thus, the grasping member 118 is always pressed vertically against the probe 119, so that it can uniformly grasp the living organism without leaving any gap. If the probe 119 is subjected to ultrasonic vibration in this state, the grasped organism is coagulated as it is incised.

In the ultrasonic coagulation-incision apparatus according to the present embodiment, as described above, the grasping member 118 moves following the deflective displacement of the ultrasonic probe 119. Therefore, the member 118 and the probe 119 can be pressed against each other without any gap between their respective contact surfaces. Thus, the same effects of the first embodiment can be obtained. According to the present embodiment, in particular, the deflection of the operating arm 113 can also ensure good contact between the grasping member 118 and the probe 119.

Figure 12:
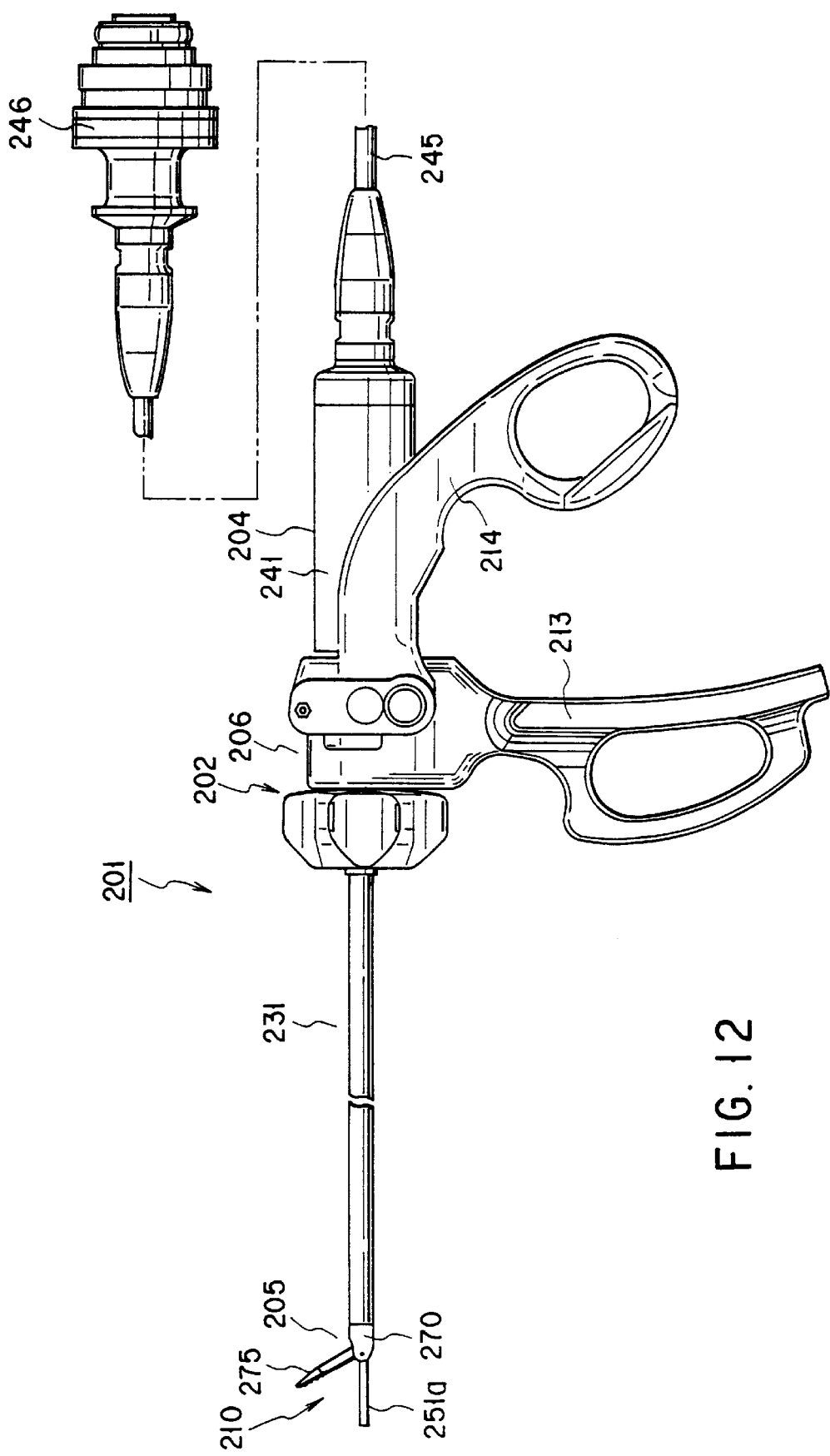
FIG. 12 is a side view showing an assembled state of an ultrasonic treatment apparatus according to a fifth embodiment of the present invention.
Figure 13:
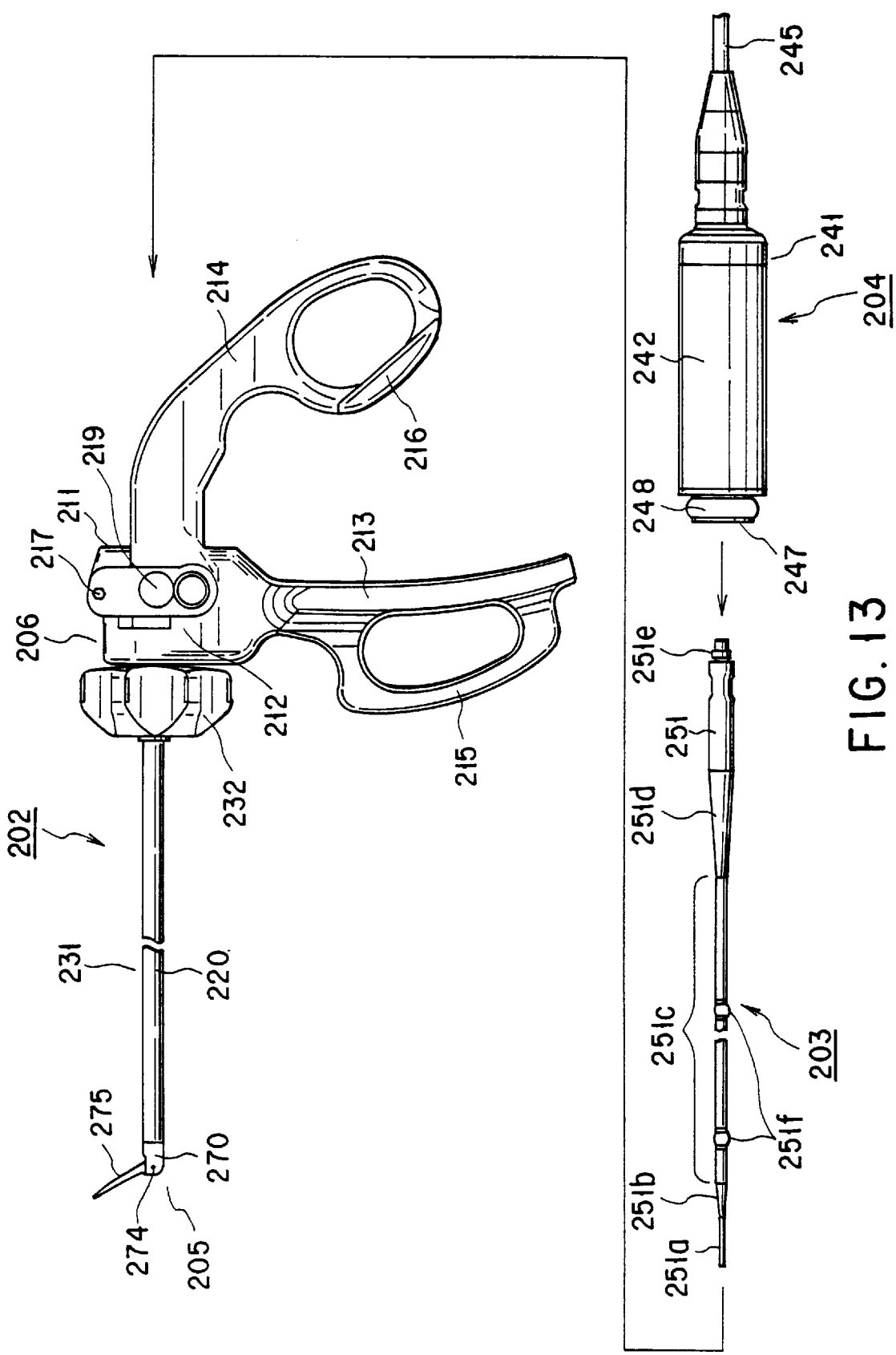
FIG. 13 is a side view showing a disassembled state of the apparatus of FIG. 12.

FIGS. 12 to 23B show a fifth embodiment of the invention. As shown in FIGS. 12 and 13, an ultrasonic treatment apparatus 201 according to the present embodiment comprises a handle unit 202, a probe unit 203, and a vibrator unit 204.

Figure 17:
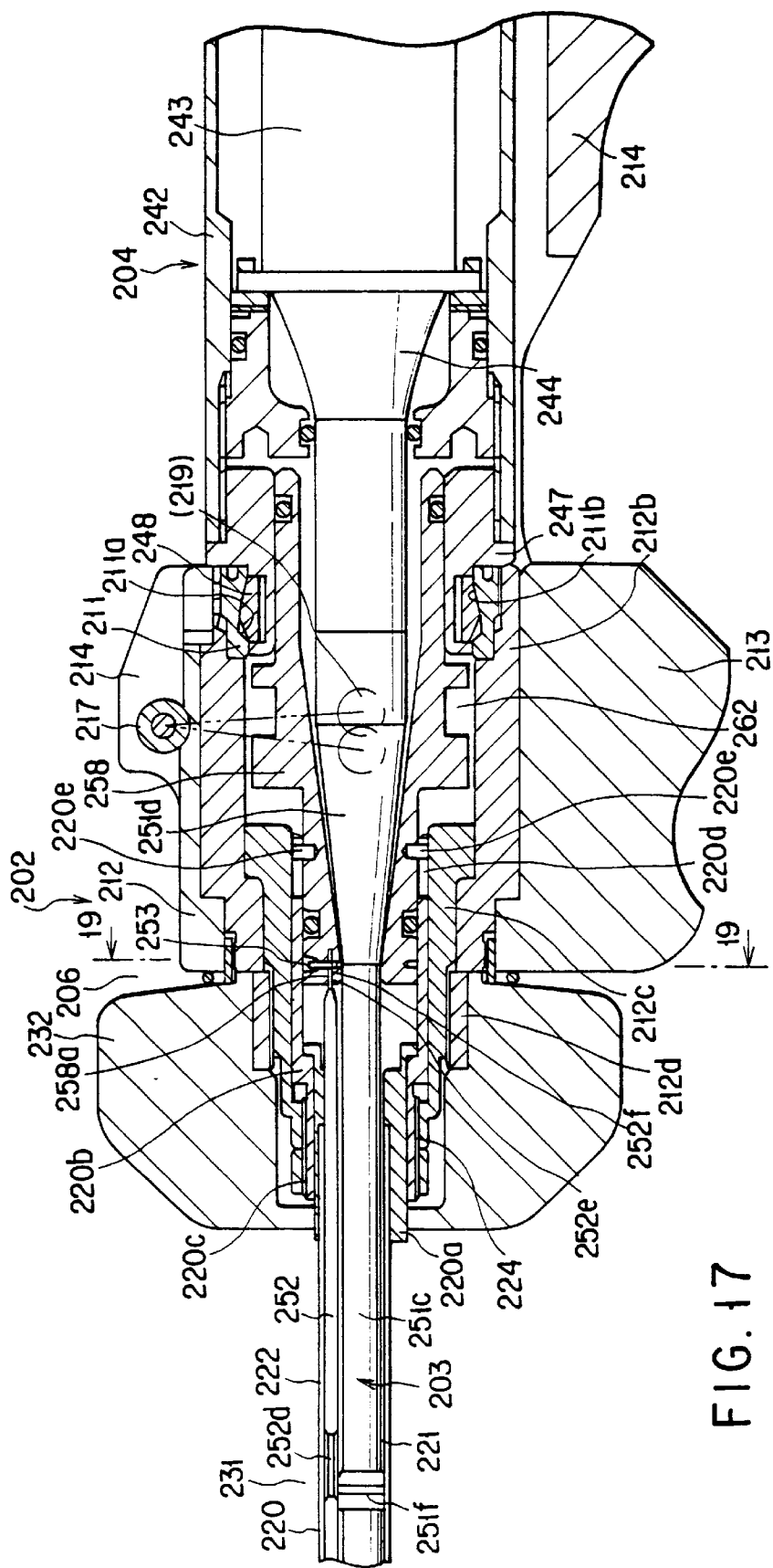
FIG. 17 is a longitudinal sectional view of the operating-section side of the apparatus of FIG. 12.

As shown in FIGS. 13 and 17, the vibrator unit 204 is formed as a hand piece 241. The hand piece 241 includes a cylindrical cover 242 that forms a grasping section. An ultrasonic transducer 243 and a horn 244 are arranged inside the cover 242. A hand piece cord 245 extends from the proximal end of the vibrator unit 204, and a hand piece plug 246 is provided on an end portion of the cord 245 (see FIG. 12). The plug 246 is connected electrically to an ultrasonic oscillator (not shown). The vibrator unit 243 is vibrated as it is supplied with electric power from the ultrasonic oscillator.

The horn 244, which is coupled to the ultrasonic transducer 243, amplifies ultrasonic vibration generated by the ultrasonic transducer 243 and enlarges its amplitude to a first phase. The distal end of the horn 244 is formed having an internal-thread portion to which the probe unit 203 is attached.

A connecting member 247 is attached to the distal end of the cover 242. The member 247 connects the vibrator unit 204, along with the probe unit 203 combined therewith, to the handle unit 202. More specifically, the connecting member 247 is provided with an engaging ring (C-shaped ring) 248 having a semicircular profile. The vibrator unit 204 is connected to the handle unit 202 as the ring 248 is caused elastically to engage an engaging groove 211a of a vibrator connecting section 211 (mentioned later) of the unit 202.

As shown in FIGS. 13, 20A and 20B, the probe unit 203 is formed as a rod-shaped vibration transmitting member 251 for transmitting the ultrasonic vibration generated by the ultrasonic transducer 243. An external-thread portion 251e to be screwed into the internal-thread portion at the distal end of the horn 244 of the vibrator unit 204 is formed on the proximal end of the transmitting member 251. The transmitting member 251 includes a proximal-side horn 251d, intermediate portion 251c, distal-side horn 251b, and columnar distal end portion 251a. The proximal-side horn 251d further enlarges the amplitude of the ultrasonic vibration, amplified by the horn 244, to a second phase. The intermediate portion 251c is situated on the distal end side of the horn 251d. The distal-side horn 251b, which is situated on the distal end side of the intermediate portion 251c, enlarges the amplitude of the ultrasonic vibration, amplified by the horn 251d, to a final phase. The distal end portion 251a is situated on the distal end side of the horn 251b (or on the distal end side of the vibration transmitting member 251).

The ultrasonic vibration from the probe ultrasonic transducer 243, amplified by the horns 244, 251d and 251b, is transmitted to the distal end portion 251a, whereupon the end portion 251a vibrates. Further, the distal end portion 251 a, along with a distal acting section 205 (mentioned later) of the handle unit 202, constitutes a treatment section 210 of the ultrasonic treatment apparatus 201.

As shown in detail in FIGS. 20A and 20B, the intermediate portion 251c is provided with a plurality of flange-shaped support pieces 251f arranged in its longitudinal direction. Each support piece 251f, which is formed of an elastic material, is situated corresponding to a node in the ultrasonic vibration transmitted through the vibration transmitting member 251. As shown in FIG. 20B, moreover, each support piece 251f is located in a shallow annular groove 218 on the outer peripheral surface of the intermediate portion 251c, and has a chevron-shaped profile (substantially in the form of an isosceles triangle having an obtuse vertical angle) such that it slightly projects outward in the diametrical direction from the outer surface of the intermediate portion 251c. Thus, the outside diameter of each support piece 251f is a little greater than that of the intermediate portion 251c. When the transmitting member 251 is in a main channel tube 221 (see FIG. 14) of an insertable sheath section 231 (mentioned later) of the handle unit 202, therefore, only the vertex of each support piece 251f is elastically pressed against inner surface of the tube 221 to keep the transmitting member 251 in the central portion of the tube 221 and prevent the member 251 and the tube 221 (sheath section 231) from coming into contact with each other (see FIGS. 17, 21 and 22A to 22I). A base portion 251g of each support piece 251f is in the form of a cylinder having an outside diameter not greater than that of the intermediate portion 251c. If the outside diameter of the base portion 251g is smaller than that of the intermediate portion 251c, in particular, the base portion 251g cannot be turned up and broken when the transmitting member 251 is inserted into the sheath section 231 or when it is wiped or rubbed to be cleaned. The support piece 251f and the groove 218 need not be annular only if they can fulfill the aforesaid functions.

As shown in FIG. 13, the handle unit 202 includes an operating section 206, the insertable sheath section 231 formed of a long sheathing tube 220 that is rotatably attached to the operating section 206, and the distal acting section 205 on the distal end of the insertable sheath section 231.

The operating section 206 includes an operating section body 212, a fixed handle 213 formed integrally with the body 212, and a movable handle 214. The operating section body 212 is provided with the vibrator connecting section 211 on its proximal end. The vibrator unit 204 is removably connected to the connecting section 211. The movable handle 214 is rockably mounted on the operating section body 212 (fixed handle 213) by means of a handle pivot 217. In this case, the handle pivot 217 is situated on the opposite side of the longitudinal central axis of the insertable sheath section 231 from the fixed handle 213. Thus, the movable handle 214 is rocked around a fulcrum that is situated above the longitudinal central axis of the sheath section 231. Further, the handle 214 has engaging pins 219 on or near the central axis of the sheath section 231. The pins 219 can engage a transmitting member 258 (see FIG. 17, mentioned later) in the operating body 212.

Figure 18:
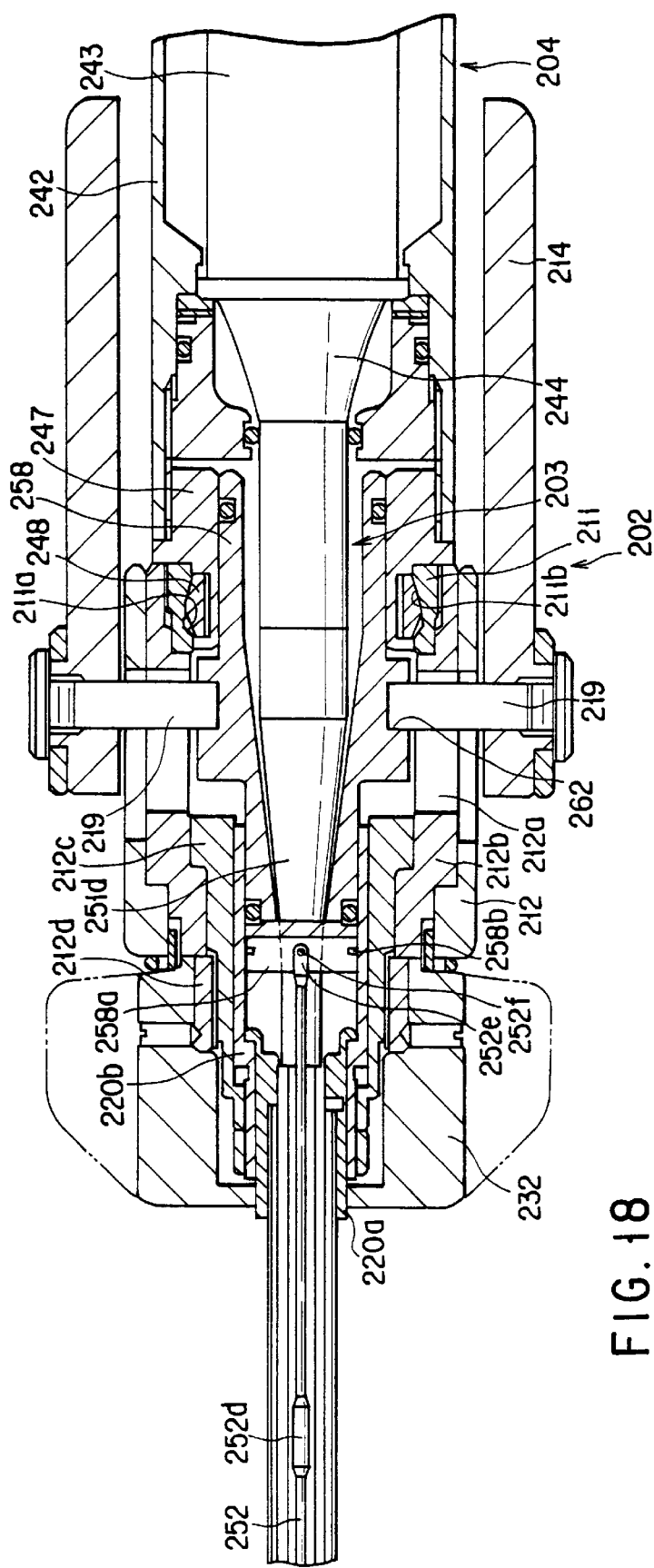
FIG. 18 is a cross-sectional view of the operating-section side of the apparatus of FIG. 12.

As shown in detail in FIGS. 17 and 18, a cylindrical interpolative member 212b is inserted and fastened in the operating section body 212. In this case, the distal end portion of the member 212b is held between a nut 212d, which is fitted in the distal end portion of the operating section body 212, and a cylindrical rotating member 212c, which is inserted and fastened in the distal end portion of the member 212b. Further, the cylindrical transmitting member (rotor) 258 is disposed inside the interpolative member 212b. The vibration transmitting member 251 is passed through a bore of the member 258. In an assembled state, the proximal-side horn 251d of the transmitting member 251 and the proximal-side portion thereof are arranged in the bore of the transmitting member 258. Moreover, an engaging groove 262 is formed on the outer peripheral surface of the transmitting member 258. Fitted in the groove 262 are the engaging pins 219 of the movable handle 214, which individually penetrate through-holes 212a in the operating section body 212 and the interpolative member 212b.

The annular vibrator connecting section 211 is attached to the inner peripheral surface of the proximal end portion of the interpolative member 212b by screwing. The engaging groove 211a is formed on the inner peripheral surface of the connecting section 211. The groove 211 has a conical engaging surface 211b on its proximal end side. The engaging surface 211b is designed to fit the curved outer peripheral surface of the engaging ring 248 that is attached to the connecting member 247 of the vibrator unit 204.

A cylindrical rotary knob 232 is attached to the nut 212d by means of a V-groove on the nut 212d and a cone-point setscrew. The proximal end portion of the sheathing tube 220 of the insertable sheath section 231 is inserted in a bore of the knob 232. An end member 220 a is fitted on the outer periphery of the proximal end portion of the tube 220 in the bore of the knob 232. The distal end portion of a connecting cylinder 220b is fitted and fixed on the outer periphery of the end member 220a by adhesive bonding. A thread portion 224 is formed on the outer peripheral surface of the distal end portion of the cylinder 220b. The distal end portion of the rotating member 212c, which extends in the bore of the rotary knob 232, is screwed on the thread portion 224. Further, the proximal end side of the connecting cylinder 220b is inserted into a bore of the rotating member 212c, and is held between the member 212c and the distal end portion of the transmitting member 258 in a manner such that it can move back and forth. The position (or longitudinal movement) of the cylinder 220b in the member 212c can be adjusted by rotating a nut 220c, which is screwed on the thread portion 224 of the cylinder 220b and engages the distal end of the member 212c. The connecting cylinder 220b has an engaging groove 220d on its proximal end. As a positioning pin 220e that protrudes from the transmitting member 258 engages the engaging groove 220d, the cylinder 220b is restrained from rotating relatively to the member 258.

As shown in FIGS. 12 and 13, the distal acting section 205 includes a holding member 270, which is attached to the distal end portion of the sheathing tube 220, and an open-close member 275 of a single-swing type, which is rockably (pivotably) attached to the member 270 by means of pivots 274. The acting section 205, along with the distal end portion 251 a of the vibration transmitting member 251 of the probe unit 203, constitutes the treatment section 210 of the ultrasonic treatment apparatus 201.

The open-close member 275 can hold a living organism in cooperation with the distal end portion 251a of the vibration transmitting member 251 so that the organism is pressed against the distal end portion 251a that is undergoing the ultrasonic vibration. Thus, vibration energy can be transmitted from the distal end portion 251a to the organism. The member 275 also functions as an exfoliating forceps for exfoliating living organisms.

As shown in FIGS. 14 to 16B, 21 and 22A to 22C, the open-close member 275 is composed of a pair of opposite side walls 275a and 275b, a proximal-side connecting portion 275c connecting the respective proximal-side upper end portions of the side walls 275a and 275b, a distal-side connecting portion 275d connecting the respective distal end portions of the side walls 275a and 275b, and attachment portions 275e extending individually downward from the respective proximal end portions of the side walls 275a and 275b.

A slit 234 is defined between the side walls 275a and 275b, and a grasping member 282 is located in the slit 234 for rocking motion. The member 282 can grasp the living organism in cooperation with the vibration transmitting member 251. More specifically, the grasping member 282 is connected integrally to a jaw 278 by means of a cylindrical collar member 277a so that the jaw 278 is held between the members 282 and 277a . Further, an attachment portion 282a of the member 282, which is situated in the slit 234, is rockably attached to the open-close member 275 by means of a pivot pin 277. In this case, the collar member 277a penetrates the attachment portion 282a of the grasping member 282 in the slit 234 and the jaw 278, while the pin 277 is passed through the member 277a . The width of the slit 234 is made greater than that of the attachment portion 282 a of the grasping member 282 that is fitted in the slit 234. As shown in detail in FIG. 16A, a given clearance X is secured between the attachment portion 282a of the member 282 and each side wall 275a or 275b, and the member 282 can move along and parallel to the pivot pin 277 for a distance corresponding to the clearance X. The distal end portion (or proximal end portion) of the grasping member 282 and the distal end portion (or proximal end portion) of the jaw 278 are connected to each other by means of a fixing pin 284 lest they be separated from each other as the open-close member 275 is moved to its open position.

The grasping member 282 includes bulging portions 282d that bulge sideways under their corresponding side walls 275a and 275b of the open-close member 275. The undersurface of the member 282 (bulging portions 282d) forms a grasping surface 282b that can grasp the organism in cooperation with the distal end portion 251a of the vibration transmitting member 251 (see FIGS. 22A and 22B). The grasping surface 282b is curved to form a recess that can receive the distal end portion 251a of the transmitting member 251. According to the present embodiment, in particular, the cross section of the surface 282b, which is perpendicular to the longitudinal direction of the grasping member 282, is in the form of a circular arc. The radius of curvature of the grasping surface 282b is greater than the radius of the distal end portion 251a of the transmitting member 251. A plurality of teeth 281 are formed on each end of the grasping surface 282b so as to be arranged in the longitudinal direction of the surface 282b.

Figure 16A:
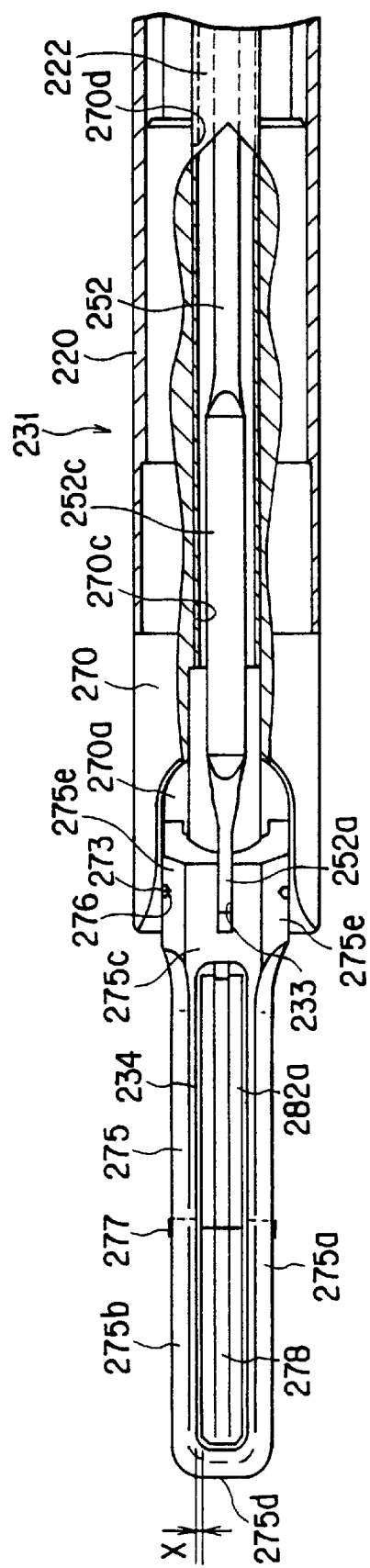
FIG. 16A is a plan view (top view), partially in section, showing the distal end side of the apparatus of FIG. 12.
Figure 16B:
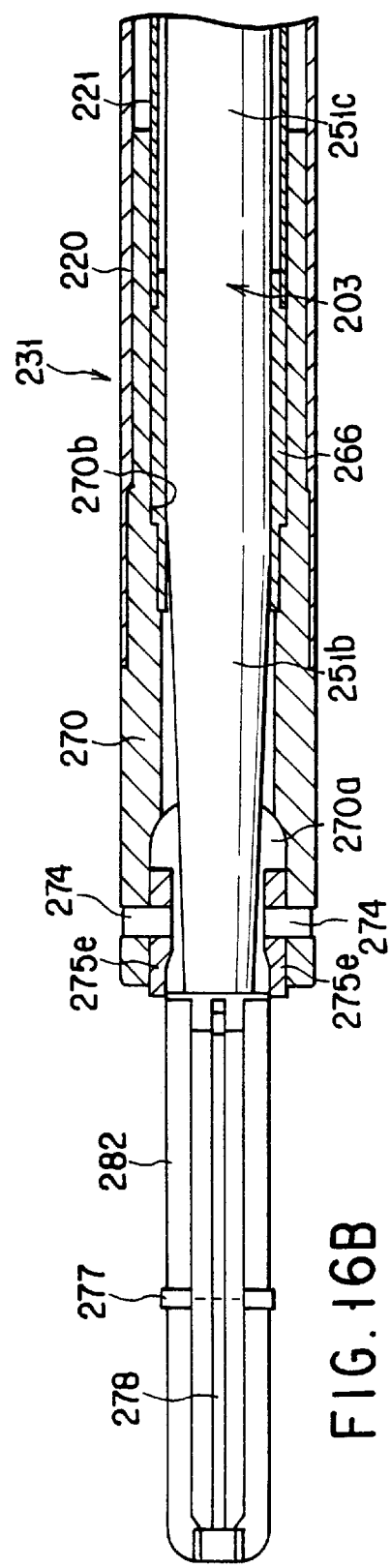
FIG. 16B is a side sectional view of the distal end side of the apparatus of FIG. 12.
Figure 22A:
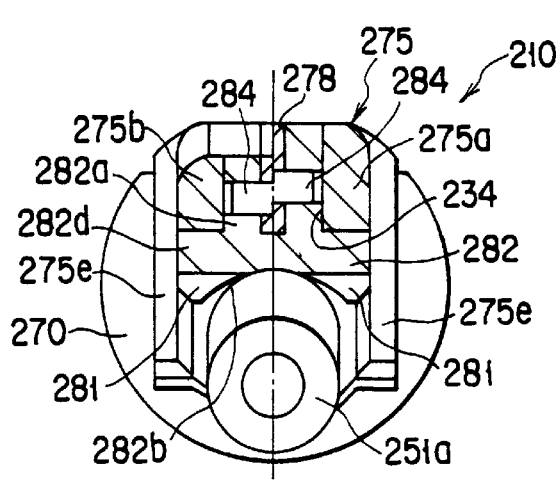
FIG. 22A is a sectional view taken along line 22A—22A of FIG. 21.
Figure 22B:
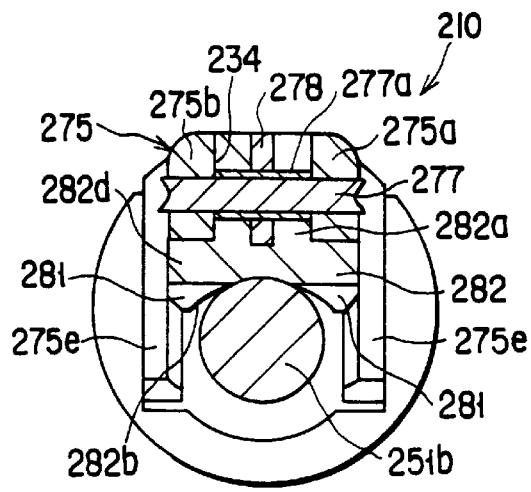
FIG. 22B is a sectional view taken along line 22B—22B of FIG. 21.
Figure 22C:
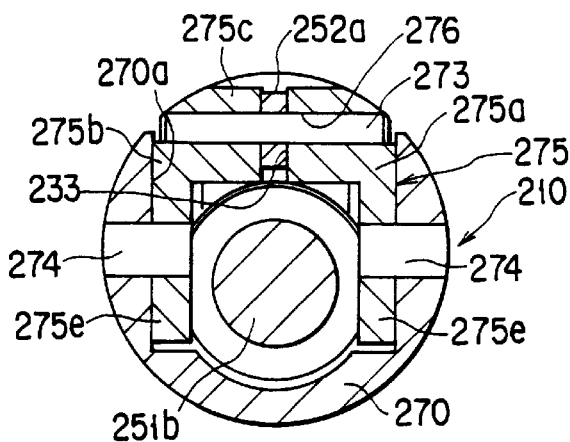
FIG. 22C is a sectional view taken along line 22C—22C of FIG. 21.
Figure 22D:
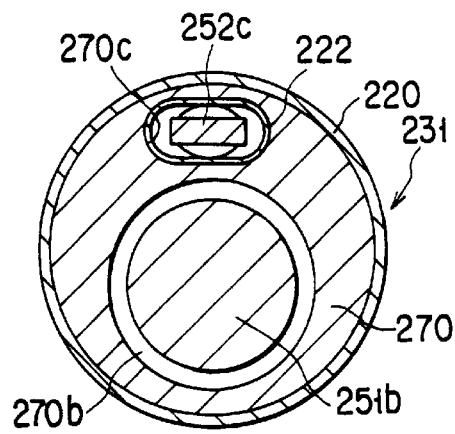
FIG. 22D is a sectional view taken along line 22D—22D of FIG. 21.

The attachment portions 275e of the open-close member 275 are fitted in a slot 270 a that is formed in the distal end of the holding member 270, and are rockably attached to the member 270 by means of the pivots 274 (see FIGS. 16A, 16B and 22C). In order to secure good strength of the holding member 270, the slot 270a opens only on the top side of the member 270 without vertically penetrating the member 270. Thus, the cross section of that region of the holding member 270 in which the slot 270a is formed is U-shaped.

The holding member 270 is formed having a main channel hole 270b, which is penetrated by the vibration transmitting member 251 of the probe unit 203, and a sub-channel hole 270c penetrated by an operating rod 252. A cylindrical spacer 266 of a low-friction material, such as Teflon, is inserted in and attached to the main channel hole 270b. A sub-channel tube 222 (mentioned later) is inserted in and attached to the sub-channel hole 270c. The spacer 266 is located in a position corresponding to the leading node in the ultrasonic vibration transmitted through the vibration transmitting member 251. The spacer 266 functions as a first support member that supports the distal end side of the transmitting member 251 from below, thereby preventing it from being substantially deflected downward by a force from the grasping member 282, when the organism is grasped by the treatment section 210.

Figure 22E:
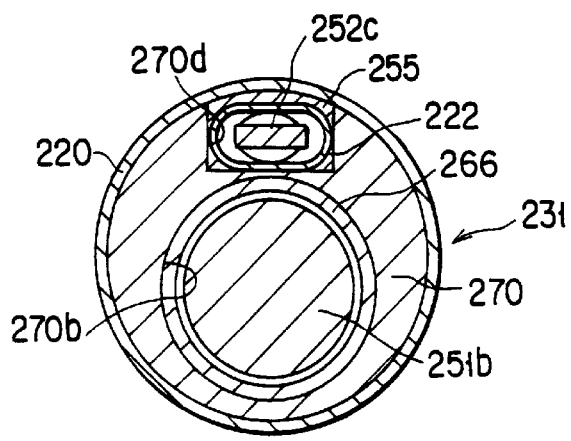
FIG. 22E is a sectional view taken along line 22E—22E of FIG. 21.
Figure 22F:
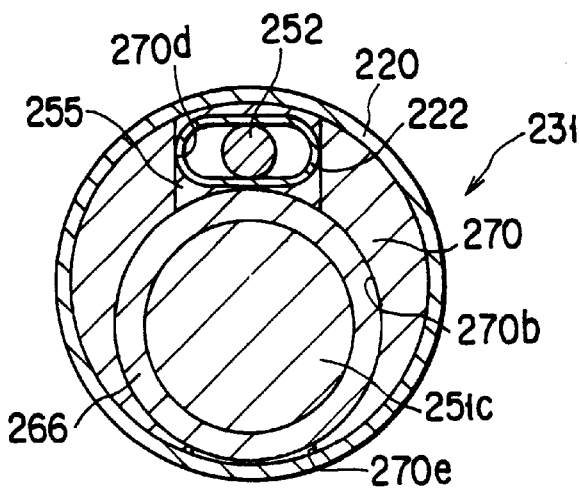
FIG. 22F is a sectional view taken along line 22F—22F of FIG. 21.

On the outer surface of the proximal end portion of the holding member 270, as shown in detail in FIGS. 22E and 22F, first and second grooves 270d and 270e, which open into the sub- and main channel holes 270c and 270b, respectively, are arranged on opposite sides facing each other. In the first groove 270d, the sub-channel tube 222 in the sub-channel hole 270c is fixed to the member 270 with an adhesive agent 255 (see FIG. 22E). Further, the proximal end side of the first groove 270d opens into the main channel hole 270b, whereby the member 270 is divided in two (see FIG. 22F). Thus, the proximal end side of the holding member 270 is divided in two by the two grooves 270d and 270e that open into the main channel hole 270b. In the position of this division, the sub-channel tube 222 and the spacer 266 are fixed in a contact state with the adhesive agent 255. The outside diameter (wall thickness) of that part of the sheathing tube which is fitted on the outer peripheral surface of the member 270 is minimized.

AS shown in FIGS. 14 to 16B, 21 and 22A to 22I, the sheathing tube 220 of the insertable sheath section 231 contains therein the main channel tube 221, which is penetrated by the vibration transmitting member 251 of the probe unit 203 is passed, and the sub-channel tube 222 for use as a rod channel through which the operating rod 252 is passed. In this case, the main channel tube 221 has a circular cross section, and is inserted into the main channel hole 270b of the holding member 270 and connected to the spacer 266. On the other hand, the sub-channel tube 222 has a cross section different from that of the rod 252, and is inserted into the sub-channel hole 270c of the member 270.

Figure 23A:
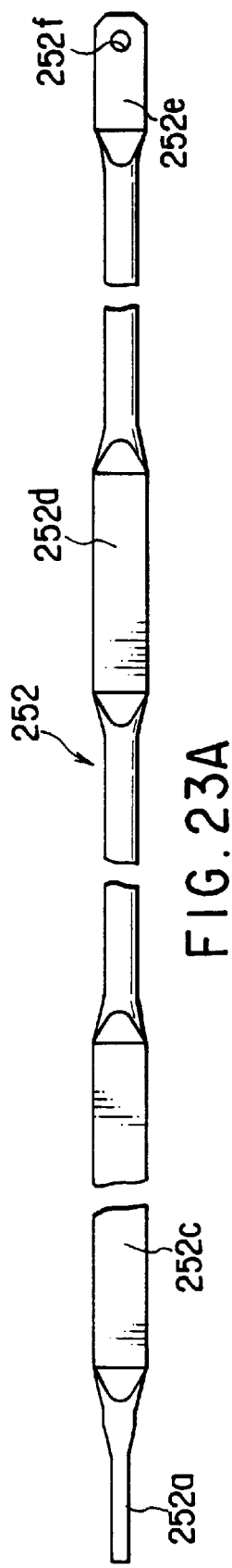
FIG. 23A is a plan view of an operating rod constituting the apparatus of FIG. 12.
Figure 23B:
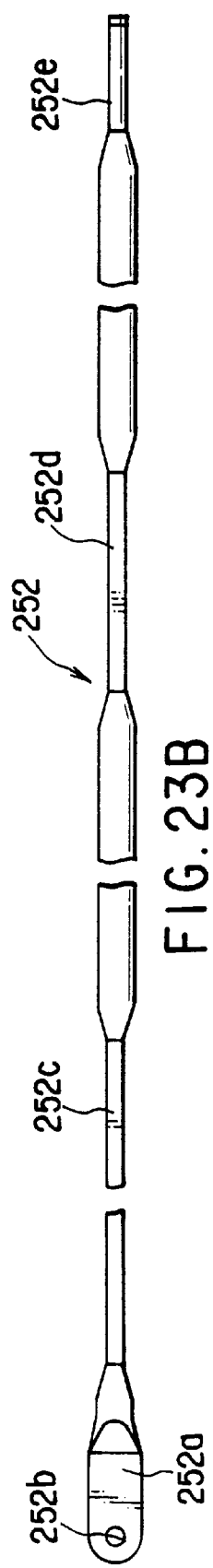
FIG. 23B is a side view of the operating rod of FIG. 23A.

As shown in FIGS. 23A and 23 B, the operating rod 252 is formed of a rod member (body portion) having a circular cross section, basically. A flat distal-end coupling portion 252a is formed on the distal end of the rod 252. The coupling portion 252a, which is obtained by laterally depressing the circular rod member, has a shaft hole 252b. Adjoining the coupling portion 252a, an elastic portion 252c is formed over a given length on the distal end side of the rod 252. The elastic portion 252c can elastically bend with ease. The portion 252c is a flat structure obtained by vertically depressing a rod member (body portion) having a circular cross section. The extending direction of a flat portion of the elastic portion 252c is perpendicular to that of a flat portion of the distal-end coupling portion 252a. The width of projection of the elastic portion 252c is a little smaller than the major axis of the sub-channel tube 222.

A flat proximal-end coupling portion 252e is formed on the proximal end of the operating rod 252. The coupling portion 252e, which is obtained by vertically depressing a rod member (body portion) having a circular cross section, has an engaging hole 252f. A plurality of bulging portions 252d are arranged at given spaces between the elastic portion 252c and the coupling portion 252e. In the present embodiment, the bulging portions 252d are located corresponding individually to the respective positions of nodes in the ultrasonic vibration transmitted through the vibration transmitting member 251. Each bulging portion 252d is obtained by vertically depressing a rod member (body portion) having a circular cross section. The width of projection of each bulging portion 252d is a little smaller than the major axis of the sub-channel tube 222.

When the operating rod 252, constructed in this manner, is in the sub-channel tube 222, only its circular-sectioned body portion is in contact with the inner surface of the tube 222. Thus, the rod 252 is held floating in the tube 222 with its elastic portion 252c and bulging portions 252d not in contact with the tube 222. On the other hand, the sub-channel tube 222 has a sectional shape different from that of the body portion of the operating rod 252. More specifically, the tube 222 has a horizontally elongated flat shape obtained by vertically depressing a tube having a circular cross section. Thus, a passage formed of a wide enough gap can be secured between the tube 222 and the rod 252, covering the overall length of the tube 222.

The distal-end coupling portion 252a of the operating rod 252 is connected to the proximal end portion of the open-close member 275. More specifically, the coupling portion 252a is inserted into a slot 233 that is formed in the proximal-side connecting portion 275c of the member 275. In this state, a pivot pin 273 is passed through an engaging hole 276, which is formed in the side walls 275a and 275b and the connecting portion 275c, and a shaft hole 252b in the distal-end coupling portion 252a, whereby the rod 252 and the member 275 are rockably connected to each other over the pivots 274. When the operating rod 252 is pushed or pulled, therefore, the open-close member 275 rocks (to be closed or opened) around the pivots 274. The respective inner surfaces of those parts of the holding member 270 in which the slot 270a is formed are situated opposite the opposite sides of the pivot pin 273. The opposed inner surfaces prevent the pin 273 from slipping off.

The proximal-end coupling portion 252e of the operating rod 252 is coupled to the distal end of the transmitting member 258 by means of an arcuate elastic C-ring 253. The member 258 is connected to the movable handle 214 by means of the engaging pins 219. More specifically, as shown in FIGS. 17 to 19, a slot 258a is formed in the distal end of the transmitting member 258, and the coupling portion 252e of the operating rod 252 is inserted in the slot 258a. An annular engaging groove 258b is formed on the outer peripheral surface of the distal end portion of the transmitting member 258, and the C-ring 253 is fitted in the groove 258b. The base portion of the engaging groove 258b is formed having a through-hole 258c that reaches the slot 258a. One end portion 253a of the C-ring 253 is inserted in the hole 258c. The one end portion 253a is bent toward the center of the circular arc of the C-ring 253, and is in engagement with the engaging hole 252f of the proximal-end coupling portion 252e of the operating rod 252 that is inserted in the slot 258a. The radius of curvature of the C-ring 253 is smaller than that of the annular base portion of the engaging groove 258b. Thus, the C-ring 253 is attached to the groove 258b without backlash in a manner such that it is elastically spread.

Figure 22G:
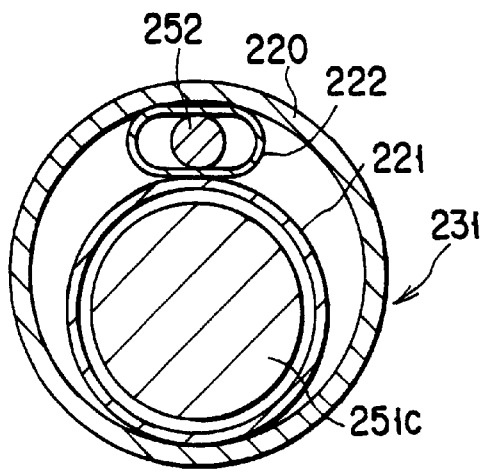
FIG. 22G is a sectional view taken along line 22G—22G of FIG. 21.
Figure 22H:
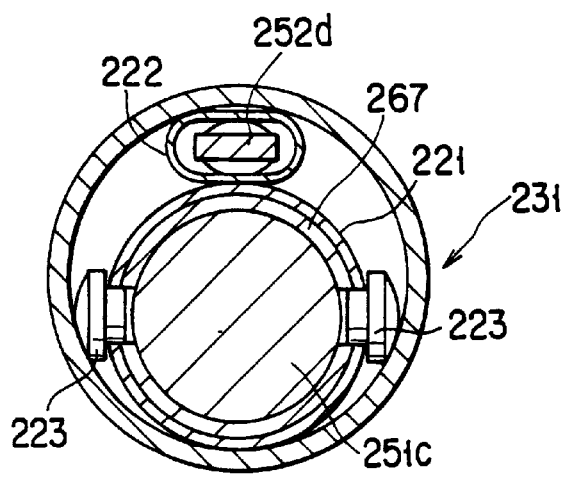
FIG. 22H is a sectional view taken along line 22H—22H of FIG. 21.
Figure 22I:
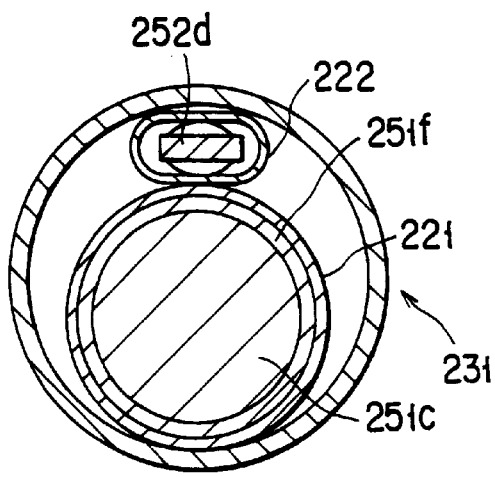
FIG. 22I is a sectional view taken along line 22I—22I of FIG. 21.

As shown in FIGS. 21 and 22H, a spacer 267 is inserted and fastened in the distal end portion of the main channel tube 221. The spacer 267 is located in a position corresponding to a node in the ultrasonic vibration transmitted through the vibration transmitting member 251, i.e., the second node next to the leading node. Thus, the spacer 267 is situated corresponding to the node adjacent to the leading node corresponding to the spacer 266. The spacer 267 functions as a second support member that supports the distal end side of the vibration transmitting member 251 from above, thereby restraining the member 251 from moving upward around a point (point of support by the spacer 266) near the leading node, when the living organism is grasped by the treatment section 210. Further, the spacer 267 is fixedly positioned with respect to the main channel tube 221 by means of two fixing pins 223 that penetrate the spacer 667 and the tube 221 on two opposite sides. In this case, the two pins 223 are horizontally opposed to each other at an angular distance of 180° in the circumferential direction. On the proximal end side with respect to the holding member 270, as shown in FIGS. 22G, 22H and 22I, the sheathing tube 220, main channel tube 221, and sub-channel tube 222 are arranged in contact with one another.

The following is a description of the operation of the ultrasonic treatment apparatus 201 constructed in this manner.

In treating an organism by means of the ultrasonic treatment apparatus 201, the organism is first situated between the grasping member 282 on the distal end of the handle unit 202 and the distal end portion 251a of the vibration transmitting member 251. Then, in this state, the fixed handle 213 is grasped, and the movable handle 214 is rocked around the handle pivot 217 to be moved forward or toward the handle 213. When the handle 214 is rocked forward in this manner, each engaging pin 219 thereon moves forward in a circular arc around the pivot 217, as indicated by broken line in FIG. 17, so that the transmitting member 258 in engagement with the pins 219 slides forward in the operating section body 212. Thereupon, the operating rod 252, which is connected to the member 258 by means of the C-ring 253, is pushed forward in the sub-channel tube 222.

In this case, the operating rod 252 has a structure including the bulging portions 252d and the circular-sectioned body portion that are alternately connected to one another in the longitudinal direction thereof. The body portion is in contact with the inner surface of the sub-channel tube 222, and each bulging portion 252d has a flat shape similar to that of the tube 222. (The width of projection of each bulging portion 252d is a little smaller than the major axis of the sub-channel tube 222.) Thus, the rod 252 is properly supported by the inner surface of the tube 222 throughout its length. As the circular-sectioned body portion, a first buckling restraining portion, touches the sub-channel tube 222, the rod 252 is restrained from moving in the vertical direction. As the bulging portions 252d, second buckling restraining portions, project in the major-axis direction of the tube 222, the rod 252 is restrained from moving from side to side. (In other words, the flat bulging portions 252d are arranged at suitable spaces in the longitudinal direction of the rod 252, in order to reduce the length of the circular-sectioned body portion that easily buckles in the flat tube 222.) Accordingly, the operating rod 252 never buckles if it is pushed out forward. The elastic portion 252c of the rod 252 also projects in the major-axis direction of the sub-channel tube 222, and has the same buckling preventing function with each bulging portion 252d.

When the operating rod 252 is thus pushed forward without buckling, the open-close member 275, which is connected to the distal end of the rod 252, rocks downward (toward the distal end portion 251a of the vibration transmitting member 251) around the pivots 274. Thereupon, the organism is held between the distal end portion 251a of the member 251 and the grasping member 282 that is rockably attached to the open-close member 275. At the same time, the distal end portion 251a of the transmitting member 251 is deflected downward by a force received from the grasping member 282, as shown in FIG. 15. As this is done, however, the member 282 rocks around the pivot pin 277 with respect to the member 275, so that it is always pressed vertically against the distal end portion 251a. At this time, moreover, the distal end portion 251a never fails to be positioned corresponding to the central portion of the grasping surface 282b of the member 282. Thus, according to the present embodiment, the distal end portion 251a is columnar, while the grasping surface 282b has the shape of a circular arc. Further, the radius of curvature of the grasping surface 282b is greater than the radius of the distal end portion 251a. Furthermore, the given clearance X is secured between the attachment portion 282a of the grasping member 282 and each side wall 275a or 275b of the open-close member 275, and the member 282 can move along the pivot pin 277 for the distance corresponding to the clearance X. If the distal end portion 251a of the vibration transmitting member 251 skews or becomes eccentric when the organism is held between itself and the grasping member 282, therefore, it is moved along the arcuate grasping surface 282b to be always positioned corresponding to the central portion of the surface 282b by a grasping force. If the eccentricity of the distal end portion 251a cannot be corrected by the contact between the two arcuate surfaces, the grasping force causes the grasping member 282 to move along and parallel to the pivot pin 277, thereby positioning the distal end portion 251a corresponding to the central portion of the grasping surface 282b.

The rocking motion of the grasping member 282 is restricted as the respective top surfaces of the bulging portions engage the undersurfaces of the side walls 275a and 275b of the open-close member 275. Preferably, therefore, rocking angle of the member 282 is adjusted to 100 or less.

Further, the two spacers 266 and 267 restrains the deflection of the distal end portion 251a of the vibration transmitting member 251 that is caused when the organism is held between the grasping member 282 and the end portion 251a. More specifically, the spacer 266, which is situated corresponding to the leading node in the ultrasonic vibration, generates an upward reaction force by supporting the distal end side of the transmitting member 251 from below when the organism is grasped by the treatment section 210. By doing this, the spacer 266 restrains the distal end portion 251a from being deflected downward. On the other hand, the spacer 267, which is situated corresponding to the second node in the ultrasonic vibration, generates a downward reaction force by supporting the distal end side of the transmitting member 251 from above when the organism is grasped by the treatment section 210. By doing this, the spacer 267 restrains the transmitting member 251 from moving upward on the proximal end side of the point of support by the spacer 266. In consequence, the spacer 267 cooperates with the spacer 266 to restrain the distal end portion 251a from being deflected downward.

When the organism is held between the grasping member 282 and the distal end portion 251a of the vibration transmitting member 251 in this manner, electric power is supplied from the ultrasonic oscillator (not shown) to the ultrasonic transducer 243, whereupon the vibrator 243 is vibrated. The ultrasonic vibration generated in the vibrator 243 is amplified by the horn 244 and transmitted to the transmitting member 251 that is connected to the horn 244. The ultrasonic vibration transmitted to the member 251 is further amplified by the horns 244, 251 d and 251 b and then transmitted to the distal end portion 251a.

In this case, the vibration transmitting member 251 has the support pieces 251f on its outer peripheral surface, which can be elastically pressed against the inner surface of the main channel tube 221 to keep the member 251 in the central portion of the tube 221 or prevent it from touching the tube 221. Thus, vibration energy can be transmitted to the distal end portion 251a without a loss. According to the present embodiment, in particular, each support piece 251f has a chevron-shaped profile and is situated corresponding to a node in the ultrasonic vibration. Therefore, the area of contact between each piece 251f and the main channel tube 221 is so small that vibration hardly produces any frictional heat between the inner surface of the tube 221 and each piece 251f. Thus, the vibration energy can be transmitted to the distal end portion 251a without any substantial loss.

The spacers 266 and 267, which come into contact with the vibration transmitting member 251 as the distal end portion 251a is deflected when the organism is grasped, are situated corresponding to the nodes in the vibration and are formed of a low-friction material such as Teflon, so that they never hinder the ultrasonic vibration of the transmitting member 251. In other words, vibration hardly produces any frictional heat between the transmitting member 251 and the spacers 266 and 267. Thus, the vibration energy can be transmitted to the distal end portion 251a without any substantial loss.

When the ultrasonic vibration is thus transmitted to the distal end portion 251a without any substantial loss, thereby vibrating the end portion 251a, the grasped organism, which is in contact with the portion 251a, is coagulated or incised with use of frictional heat that is produced by the ultrasonic vibration. In this case, the grasping member 282 is pressed against the distal end portion 251a at right angles thereto by the aforesaid rocking motion, so that the organism can be securely coagulated or incised throughout the length of the member 282. Further, the grasping surface 282b and the distal end portion 251a, having the shape of a circular arc each, share a narrow contact surface, so that load for each unit area is heavy, and normal drag for friction is substantial. Thus, frictional heat can be effectively produced to improve the coagulation-incision capacity.

If necessary, the insertable sheath section 231 can be rotated relatively to the operating section 206 during treatment. When the rotary knob 232 is turned, the rotating member 212c, which is connected to the knob 232, the transmitting member 258, which is nonrotatably fixed by means of the positioning pin 220e to the connecting cylinder 220b that is screwed in the rotating member 212c, and the sheathing tube 220, which is connected to the cylinder 220b, rotate in one united body. In this case, the operating rod 252, which is connected to the transmitting member 258, also rotates together with the member 258 (sheathing tube 220), so that it can be prevented from being twisted in the tube 220. In general, moreover, if the distal end portion 251a of the vibration transmitting member 251 is eccentric or skewed, the way of its engagement with the grasping surface 282b of the grasping member 282 varies to change the state of the grasped organism when the sheath section 31 is rotated relatively to the operating section 206. According to the present embodiment, however, the distal end portion 251a is always positioned corresponding to the central portion of the grasping surface 282b of the grasping member 282, as mentioned before, so that the organism can be treated with good stability and high efficiency. Moreover, the open-close member 275 can be used as a separator for separating the living organism. In this case, the organism touches the respective back surfaces (top surfaces) of the member 275, jaw 278, and grasping member 282, so the rocking motion of the member 282 never influences the separating operation.

When the treatment of the organism is completed in this manner, the movable handle 214 is rocked back to pull the operating rod 252. Thereupon, the open-close member 275 rocks upward (or away from the distal end portion 251a of the vibration transmitting member 251) around the pivots 274 to release the end portion 251a from the force of pressure. As this is done, the distal-end coupling portion 252a of the rod 252 moves downward in a circular arc. This movement pulls the whole rod 252 downward. Since the elastic portion 252c is curved by elastic deformation, however, only the distal end portion of the rod 252 moves. In this case, moreover, the elastic portion 252c never interferes with the sub-channel tube 222, since it has a flat shape such that a gap wide enough is formed between itself and the tube 222.

In cleaning the ultrasonic treatment apparatus 201 after use, on the other hand, the apparatus 201 is disassembled into three parts, the handle unit 202, probe unit 203, and vibrator unit 204. In doing this, the probe unit 203 and the vibrator unit 204 are first removed together from the handle unit 202 and then separated from each other.

In cleaning the main channel tube 221, the probe unit 203 is disengaged from the operating section 206 of the handle unit 202 to open the tube 221, and a cleaning fluid is flushed through the opened tube 221 or a brush is inserted into the tube 221. If the probe unit 203 is removed from the handle unit 202, the sub-channel tube 222 is also opened. Accordingly, the tube 222 can be also cleaned by being flushed with the cleaning fluid. In this case, the operating rod 252 is kept inserted in the sub-channel tube 222. However, the rod 252 is held floating in the tube 222 with only its circular-sectioned body portion in contact with the inner surface of the flat tube 222 and with its elastic portion 252c and bulging portions 252d not in contact with the tube 222. Therefore, a passage or gap wide enough for cleaning can be secured between the tube 222 and the rod 252 throughout the length of the tube 222. Thus, the cleaning fluid introduced into the sub-channel tube 222 can flow covering the overall length of the tube 222, thereby securely cleaning the tube 222.

In the ultrasonic treatment apparatus 201 according to the present embodiment, as described above, the grasping member 282 moves following the deflective displacement of the distal end portion 251a of the vibration transmitting member 251. Therefore, the member 282 and the end portion 251a can be pressed against each other without any gap between their respective contact surfaces. Thus, satisfactory coagulation-incision capacity can be secured throughout the respective contact surfaces of the member 282 and the end portion 251a. Further, the rocking motion of the grasping member 282 is restricted to a minimum range such that the deflection of the distal end portion can be absorbed as the respective top surfaces of the bulging portions 282d of the member 282 engage the respective undersurfaces of the side walls 275a and 275b of the open-close member 275. In consequence, the grasping member 282 never undergoes an unreasonable backlash.

In the ultrasonic treatment apparatus 201 of the present embodiment, moreover, the wide passage for the cleaning fluid is formed between the operating rod 252 and the sub-channel tube 222 penetrated thereby, and the rod 252 can be prevented from buckling.

If the respective cross sections of the operating rod and the channel that is penetrated by the rod have the same shape, in general, there is no gap between the rod and the channel, so that the interior of the channel can be cleaned. If a wide gap is formed between the channel and the operating rod, it causes the rod inevitably to buckle as the rod is pushed forward in the channel. However, these problems can be solved by differently shaping the respective cross sections of the channel and the rod and properly supporting the rod by means of the inner surface of the sub-channel tube 222.

Thus, according to the present embodiment, the sub-channel tube 222 has a flat shape, and the operating rod 252 has the structure including the bulging portions 252d and the circular-sectioned body portion that are alternately connected to one another in the longitudinal direction thereof. Only the body portion is in contact with the inner surface of the tube 222, while the elastic portion 252c and the bulging portions 252d project in the major-axis direction of the tube 222 and are held floating in the tube 222 without touching it. Thus, the passage for cleaning can be secured between the tube 222 and the rod 252 throughout the length of the tube 222. Further, the vertical movement of the rod 252 is restrained by the body portion that is in contact with the tube 222, while the lateral movement of the rod 252 is restrained by the elastic portion 252c and the bulging portions 252d that project in the major-axis direction of the tube 222. In consequence, the operating rod 252 is prevented from buckling.

Since the sub-channel tube 222 is flat, moreover, the main and sub-channel tubes 221 and 222 can be arranged efficiently in the sheathing tube 220 without lowering the efficiency of cleaning in the tube 222 and the strength of the vibration transmitting member 251. Thus, the inside diameter of the main channel tube 221, which is penetrated by the transmitting member 251, can be increased to allow a greater outside diameter for the member 251 without failing to secure the passage wide enough for cleaning in the sub-channel tube 222. Further, the operating force of the operating rod 252 can never be transmitted to the transmitting member 251.

Although the bulging portions 252d of the operating rod 252 according to the present embodiment are situated corresponding individually to the nodes in the ultrasonic vibration, the present invention is not limited to this arrangement. Moreover, the bulging portions 252d may be reduced in number by enhancing the rigidity of the operating rod 252.

In the ultrasonic treatment apparatus 201 according to the present embodiment, furthermore, the deflection of the distal end portion. 251a of the vibration transmitting member 251, holding an organism between itself and the grasping member 282, can be restrained by the two spacers 266 and 267 that are located corresponding to the leading and second nodes in the ultrasonic vibration, respectively. Thus, the deflection of the transmitting member 251 can be effectively restrained by individually locating the first and second support members 266 and 267, which generate reaction forces against the deflection of the member 251, in positions where substantial lateral forces are received, that is, positions where the deflected member 251 abuts against the lower and upper surfaces of the main channel tube 221. Accordingly, production of frictional heat (loss of vibration energy) attributable to the contact between deflected transmitting member 251 and the tube 221 can be restrained, and the organism can be firmly held between the distal end portion 251a and the grasping member 282 and securely coagulated or incised. In this connection, if the transmitting member 251 is supported by means of an elastic material in positions corresponding to the leading and second nodes in the ultrasonic vibration, the elastic material, which is easily deformable, cannot effectively prevent the deflection of the member 251.

According to the present embodiment, moreover, the spacers 266 and 267 are situated corresponding to the nodes in the ultrasonic vibration and are formed of a low-friction material such as Teflon. Therefore, the ultrasonic vibration cannot be hindered by the spacers 266 and 267 that are in contact with the vibration transmitting member 251. In other words, vibration hardly produces any frictional heat between the transmitting member 251 and the spacers 266 and 267. Thus, the vibration energy can be transmitted to the distal end portion 251a without any substantial loss.

According to the present embodiment, furthermore, the outer peripheral surface of the vibration transmitting member 251 is provided with the support pieces 251f, which can hold the member 251 in the central portion of the main channel tube 221, thereby preventing contact between the member 251 and the tube 221. Besides, the support pieces 251f are elastic members having a chevron-shaped profile and are situated corresponding individually to a third node and its subsequent nodes in the vibration that are not subjected to any substantial lateral forces. Thus, the manufacturing cost can be made lower than in the case where spacers of Teflon, a low-friction material, are arranged in positions corresponding to all the nodes in the vibration. Further, the area of contact between the inner surface of the main channel tube 221 and each support piece 251f can be reduced, so that production of frictional heat by vibration between these elements can be restrained. (The vibration energy can be transmitted to the distal end portion 251a without any substantial loss.) Since each support piece 251f is an elastic member, moreover, it can be easily attached to the vibration transmitting member 251, and a high vibration-damping effect (effect to absorb vibration) can be obtained.

In the ultrasonic treatment apparatus 201 according to the present embodiment, moreover, the distal end portion 251a can always be positioned corresponding to the central portion of the grasping surface 282b of the grasping member 282. Thus, according to the present embodiment, the distal end portion 251a of the vibration transmitting member 251 is columnar, while the grasping surface 282b has the shape of a circular arc. Further, the radius of curvature of the grasping surface 282b is greater than the radius of the distal end portion 251a. Furthermore, the given clearance X is secured between the attachment portion 282a of the grasping member 282 and each side wall 275a or 275b of the open-close member 275, and the member 282 can move along the pivot pin 277 for the distance corresponding to the clearance X. If the distal end portion 251a of the vibration transmitting member 251 skews or becomes eccentric when the organism is held between itself and the grasping member 282, therefore, it is moved along the arcuate grasping surface 282b to be always positioned corresponding to the central portion of the surface 282b by the grasping force. If the eccentricity of the distal end portion 251a cannot be corrected by the contact between the two arcuate surfaces, the grasping force causes the grasping member 282 to move along and parallel to the pivot pin 277, thereby positioning the distal end portion 251a corresponding to the central portion of the grasping surface 282b. Thereupon, the treatment section 210 can be kept satisfactorily in contact with the organism, so that it can securely grasp the organism and treat it with good stability and high efficiency.

According to the present embodiment, moreover, the radius of curvature of the grasping surface 282b is greater than the radius of the distal end portion 251a.

Alternatively, however, these radii may be set at substantially equal values.

In the ultrasonic treatment apparatus 201 according to the present embodiment, furthermore, the operating rod 252 and the open-close member 275 are rockably connected to each other over the pivots 274, a fulcrum for the rocking motion of the member 275. When the rod 252 is pushed out forward, the member 275 is rocked downward, whereupon the treatment section 210 is closed. Thus, a link mechanism of the treatment section 210 is designed so that the open-close member 275 is rocked downward as the operating rod 252 is pushed out forward. Accordingly, the pivots 274 can be supported inside the insertable sheath section 231 (holding member 270), not on the outer peripheral portion thereof, so that the strength and durability of the distal acting section 205 can be kept high enough, and a good length can be secured for the link.

According to the present embodiment, moreover, the movable handle 214 is provided as a mechanism for moving the operating rod 252, and a point of action or input portion (engaging portion between each engaging pin 219 and the transmitting member 258) for the operating force on the rod 252 is situated between the handle pivot 217, which serves as a fulcrum for the rocking motion of the handle 214, and a finger plate portion 216 of the handle 214 as a point of application to which the operating force is applied. More specifically, the pivot 217 is located above the longitudinal central axis of the insertable sheath section 231. Further, the engaging pins 219, which engage the transmitting member 258, are fixed to the movable handle 214, on or near the central axis of the sheath section 231, and the handle 214 extends below the sheath section 231, thus forming the finger plate portion 216. When the handle 214 is advanced, therefore, the engaging pins 219 move forward in a circular arc around the handle pivot 217. As this is done, the operating rod 252 is pushed forward in the sub-channel tube 222. Accordingly, it is unnecessary to provide any link mechanism for aligning the operating direction for the movable handle 214 with the moving direction of the rod 252. Thus, no frictional resistance is produced at the fulcrum of the link or each end of the link by the transmission of force. As the number of kinematic pairs of the link is reduced, moreover, regions that require necessary gaps for operation are reduced, so that backlash lessens as a whole. As the number of required members is reduced, furthermore, regions that are subject to elastic deformation are also reduced, so that the general elastic deformation lessens. These effects ensure accurate correspondence between handle manipulation and the action of the treatment section 210 at the distal end and improved feeling of manipulation. Since the overall length of the movable handle 214 is equal to the distance from the fulcrum to the point of application of a lever, moreover, a great operating force (torque) can be generated by effectively utilizing the limited length of the handle 214. Since a satisfactory operating force can be generated even if the handle 214 is miniaturized, the handle 214 less frequently interferes with a patient's body during the treatment. Thus, the operability and safety of the apparatus can be improved. Further, the trajectory of rotation of the finger plate portion 216 during the rocking motion of the movable handle 214 is a large-radius circular arc that is substantially coincident with the trace of a linear motion of a finger on the plate portion 216, so that the handle 214 can be manipulated smoothly.

These characteristics of the movable handle 214 serve favorably for the ultrasonic treatment apparatus 201. Thus, in this treatment apparatus, the vibrator unit 204 inevitably projects behind the movable handle 214. If the fulcrum for the rocking motion of the handle 214 is situated below the vibrator unit 204, therefore, the handle 214 approaches the unit 204 so that an operator's hand and the unit 204 can easily interfere with each other when the handle 214 is swung wide open. In the arrangement according to the present embodiment, on the other hand, the movable handle 214 moves rearward in a large-radius circular arc, so that the space between the handle 214 and the unit 204 cannot be reduced much. In consequence, the operator's hand less frequently interferes with the vibrator unit 204, so that the operability is improved.

Figure 24A:
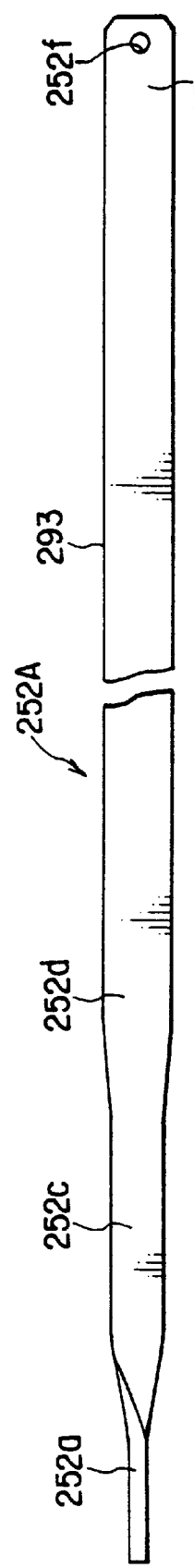
FIG. 24A is a plan view of an operating rod according to a modification.
Figure 24B:
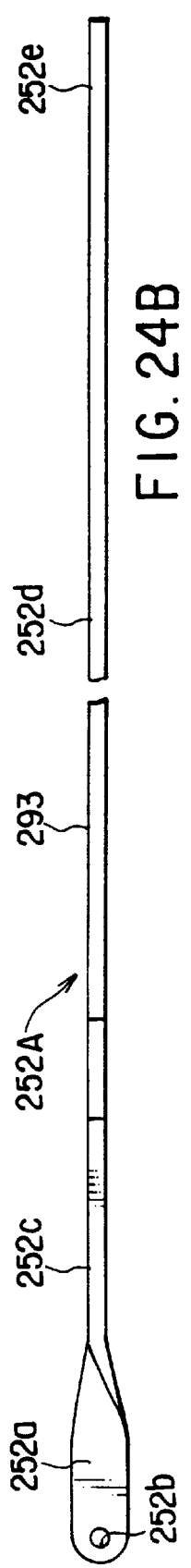
FIG. 24B is a side view of the operating rod of FIG. 24A.

FIGS. 24A and 24B show a modification of the operating rod. In FIGS. 24A and 24B and in the description to follow, the same components of the fifth embodiment are designated by like numerals for simplicity.

As shown in FIGS. 24A and 24B, an operating rod 252A according to this modification is formed of a belt-shaped plate material 293. In order to form the distal-end coupling portion 252a that is connected to the open-close member 275, the distal end portion of the plate material 293 is twisted at 90°. The width of the distal end portion of the plate material 293 is equal to that of the coupling portion 252a, while the width of the other part of the plate material 293 than the distal end portion is equal to that of the proximal-end coupling portion 252e that is connected to the transmitting member 258. With use of this arrangement, the same functions and effects of the operating rod 252 according to the foregoing embodiment can be obtained. Since the construction of the apparatus can be simplified, moreover, the manufacturing cost can be lowered.

FIGS. 25A to 25C show a modification of the distal acting section. In FIGS. 25A and 25B and in the description to follow, the same components of the fifth embodiment are designated by like numerals for simplicity.

In a distal acting section 205A according to this modification, as shown in FIGS. 25A and 25B, the proximal-side connecting portion 275c of the open-close member 275 extends close to the pivot pin 277. As shown in FIG. 25C, moreover, the attachment portion 282a of the grasping member 282 is fitted in the slit 234 of the member 275 in a manner such that it is held between a pair of jaws 278. According to this arrangement, the strength of that part of the open-close member 275 which supports the pin 277 is enhanced by the proximal-side connecting portion 275c that extends close to the pin 277. Thus, the collar member 277a shown in FIG. 22B is unnecessary, so that machining the components is easy.

FIGS. 26A and 26B show a first modification of the way of attaching the spacer 267 to the main channel tube 221. In FIGS. 26A and 26B and in the description to follow, the same components of the fifth embodiment are designated by like numerals for simplicity.

As shown in FIG. 26B, a main channel tube 221A according to this modification has a tongue-shaped stopper piece 221a, which is formed by cutting a U-shaped notch in part of the outer peripheral surface of the tube. The piece 221a is elastically urged to be bent inward. As shown in FIG. 26A, on the other hand, an annular engaging groove 267a is formed on the outer peripheral surface of the spacer 267.

In attaching the spacer 267 to the main channel tube 221, the spacer 267 is first inserted into the tube 221. When the spacer 267 is inserted into that part of the tube 221 which is formed having the stopper piece 221a, the outer peripheral surface of the spacer 267 urges the piece 221a diametrically outward to push it out. When the spacer 267 reaches a position in which the engaging groove 267a meets the stopper piece 221a, however, the piece 221a elastically engages the groove 267a, thereby axially positioning the spacer 267 in the tube 221. The main channel tube 221 is sealed to be isolated from the outside by packing a space between the piece 221a and the groove 267a with an adhesive agent or sealant.

With use of this arrangement, the spacer 267 can be easily incorporated in the main channel tube 221.

FIG. 27 shows a second modification of the way of attaching the spacer 267 to the main channel tube 221. In FIG. 27 and in the description to follow, the same components of the fifth embodiment are designated by like numerals for simplicity.

According to this modification, the spacer 267, like that of the foregoing embodiment, is fixedly positioned with respect to the main channel tube 221 by means of two fixing pins 223A that individually penetrate engaging holes 267b in the spacer 267 and the tube 221. In this case, the two pins 223A (holes 267b) are arranged at an angular distance of 90° in the circumferential direction in positions above the central axis of the main channel tube 221. In this modification, moreover, the head of each fixing pin is greater than that of the foregoing embodiment and is in contact with the inner surface of the sheathing tube 220.

Since the fixing pins 223A in this arrangement are large-sized, they can be machined and handled with ease. The pins 223A may be also used to position the sheathing tube 220, main channel tube 221, and sub-channel tube 222 (so with the fifth embodiment), thus facilitating assembly operation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment apparatus comprising:
   an ultrasonic transducer for generating ultrasonic vibration;
   a vibration transmitting member for transmitting the ultrasonic vibration generated by the ultrasonic transducer, the vibration transmitting member having a proximal end connected to the ultrasonic transducer and a distal end portion used to treat a living organism by means of the transmitted ultrasonic vibration;
   a grasping member opposed to the distal end portion of the vibration transmitting member and having a grasping surface capable of grasping the living organism in cooperation with the distal end portion;
   an operating mechanism for moving the grasping member between a closed position in which the grasping member engages the distal end portion of the vibration transmitting member and an open position in which the grasping member is separated from distal end portion; and
   a follow-up mechanism for driving or allowing the grasping member in the closed position to follow a deflective displacement of the distal end portion of the vibration transmitting member so that the substantially whole surface of the grasping surface of the grasping member contacts with the distal end portion of the vibration transmitting member.

2. An ultrasonic treatment apparatus according to claim 1, which further comprises a restricting mechanism for restricting the follow-up movement of the grasping member within a given range.

3. An ultrasonic treatment apparatus according to claim 1, wherein said follow-up mechanism includes an open-close member supporting the grasping member and connected to the operating mechanism and a mechanism for allowing the grasping member and the open-close member to move relative to each other, and said open-close member is operated by the operating mechanism so that the grasping member is moved between the open position and the closed position.

4. An ultrasonic treatment apparatus according to claim 1, wherein said follow-up mechanism includes an open-close member rockably supporting the grasping member for rocking motion and connected to the operating mechanism to be pivoted thereby, and said grasping member is moved between the open position and the closed position as the open-close member is pivoted by the operating mechanism.

5. An ultrasonic treatment apparatus according to claim 4, wherein said open-close member is pivotably attached to a holding member extending from the vibration transmitting member, the holding member being connected to the vibration transmitting member at a position corresponding to a node in the ultrasonic vibration transmitted through the vibration transmitting member.

6. An ultrasonic treatment apparatus according to claim 4, which further comprises a sheath penetrated by the vibration transmitting member, and wherein the distal end portion of said vibration transmitting member projects from the distal end of the sheath and said open-close member is pivotably mounted on the distal end of the sheath.

7. An ultrasonic treatment apparatus according to claim 3, wherein said mechanism for allowing the relative movement of the grasping member and the open-close member includes a spherical engaging portion provided on one of the two members and a spherical receiving portion provided on the other member and capable of receiving and engaging the engaging portion.

8. An ultrasonic treatment apparatus according to claim 3, which further comprises a restricting mechanism for restricting the relative movement of the grasping member and the open-close member.

9. An ultrasonic treatment apparatus according to claim 4, which further comprises a rocking restricting mechanism for restricting the rocking motion of the grasping member within a given range, the rocking restricting mechanism including a slot of a given length formed in one of the two associated members, the open-close member and the grasping member, and an engaging pin provided on the other member and capable of engaging the slot.

10. An ultrasonic treatment apparatus according to claim 4, wherein a clearance is secured between said grasping member and said open-close member such that the grasping member is allowed to rock within a given range and is restrained from rocking as the grasping member abuts against the open-close member.

11. An ultrasonic treatment apparatus according to claim 4, wherein the rocking angle of said grasping member is not greater than 10°.

12. An ultrasonic treatment apparatus according to claim 4, which further comprises a sheath penetrated by the vibration transmitting member and having a distal opening portion through which the distal end portion of the vibration transmitting member projects, and wherein said operating mechanism includes a fixed handle provided on the proximal end of the sheath, a movable handle pivotably attached to the fixed handle and adapted to approach the fixed handle as the movable handle pivots forward to the distal end of the sheath, and an operating rod connecting the movable handle and the open-close member and passed through the sheath, the point of action at which an operating force from the movable handle is applied to the operating rod being situated between a fulcrum for the pivoting motion of the movable handle and a finger loop portion of the movable handle serving as a point of application to which the operating force is applied, the operating rod being connected to the open-close member so that the grasping member moves to the closed position as the operating rod is pushed out to the distal end side in the sheath by means of the operating force.

13. An ultrasonic treatment apparatus according to claim 1, which further comprises a sheath penetrated by the vibration transmitting member and having a distal opening portion through which the distal end portion of the vibration transmitting member projects, a first support member located in the sheath and adapted to support a distal end side portion of the vibration transmitting member in the sheath when the distal end portion of the vibration transmitting member projecting through the distal opening portion of the sheath is deflected in a first direction, thereby restraining the distal end portion of the vibration transmitting member from deflecting in the first direction, and a second support member located in the sheath and adapted to support a distal end side portion of the vibration transmitting member in the sheath when the distal end portion of the vibration transmitting member is deflected in the first direction, thereby restraining the vibration transmitting member from moving in a second direction opposite to the first direction on the proximal end side of a point of support by the first support member, and wherein said first support member is formed of a low-friction material and situated in a position corresponding to a first node of the ultrasonic vibration transmitted through the vibration transmitting member, said first node being one nearest the distal end portion of the vibration transmitting member, and said second support member is formed of a low-friction material and situated in a position corresponding to a second node of the ultrasonic vibration, which is next to the first node.

14. An ultrasonic treatment apparatus according to claim 13, wherein said vibration transmitting member has on the outer peripheral surface thereof at least one annular support piece for preventing contact between the vibration transmitting member and the sheath by touching the sheath, the support piece being formed of an elastic material and situated in predetermined positions corresponding to other nodes than the first and second nodes in the ultrasonic vibration transmitted through the vibration transmitting member.

15. An ultrasonic treatment apparatus according to claim 14, wherein said support piece has a chevron-shaped cross section taken along an axis of the vibration transmitting member, only the obtuse vertex portion of the support piece being in contact with the sheath.

16. An ultrasonic treatment apparatus according to claim 15, wherein said support piece is situated in an annular groove formed on the outer peripheral surface of the vibration transmitting member.

17. An ultrasonic treatment apparatus according to claim 16, wherein said support piece includes a chevron-shaped body portion and a cylindrical portion forming the base of the body portion, the body portion projecting out from the annular groove, the cylinder portion having an outside diameter smaller than that of that part of the vibration transmitting member on which the annular groove is not formed and being situated inside the annular groove.

18. An ultrasonic treatment apparatus according to claim 3, which further comprises a sheath penetrated by the vibration transmitting member and having a distal opening portion through which the distal end portion of the vibration transmitting member projects and a rod channel provided in the sheath, and wherein said operating mechanism includes an operating rod passed through the rod channel, connected to the open-close member, and adapted to operate the open-close member as it is moved in the rod channel, the cross section of the rod channel having a shape different from that of the operating rod so that a continuous passage for a fluid is formed between the operating rod and the rod channel throughout the length of thereof.

19. An ultrasonic treatment apparatus according to claim 18, wherein the cross section of said rod channel has a flat shape obtained by depressing a circle diametrically inward from two opposite sides thereof.

20. An ultrasonic treatment apparatus according to claim 19, wherein said operating rod is formed of a body member having a circular cross section and has a buckling restraining portion on at least a part thereof for restraining the operating rod from buckling in the rod channel, the buckling restraining portion being formed flat by depressing the body member in a direction perpendicular to the axial direction from two opposite sides thereof in a predetermined position.

21. An ultrasonic treatment apparatus according to claim 20, wherein a plurality of buckling restraining portions are arranged at given spaces in the longitudinal direction of the body member of the operating rod.

22. An ultrasonic treatment apparatus according to claim 1, wherein the distal end portion of said vibration transmitting member is columnar, and the grasping surface of said grasping member is curved to form a recess for receiving the distal end portion of the vibration transmitting member.

23. An ultrasonic treatment apparatus according to claim 22, wherein the grasping surface of said grasping member has an arcuate profile on a cross section perpendicular to the longitudinal direction of the grasping member and a radius of curvature substantially equal to or greater than the radius of the distal end portion of the vibration transmitting member.

24. An ultrasonic treatment apparatus according to claim 22, wherein said grasping member is movable along a support shaft supporting the grasping member for rocking motion with respect to the open-close member.

* * * * *